United States Patent
Li et al.

(10) Patent No.: US 10,465,147 B2
(45) Date of Patent: Nov. 5, 2019

(54) COPOLYMERS

(71) Applicants: Jun Li, Singapore (SG); Zhongxing Zhang, Singapore (SG); Xian Jun Loh, Singapore (SG); Xiping Ni, Singapore (SG)

(72) Inventors: Jun Li, Singapore (SG); Zhongxing Zhang, Singapore (SG); Xian Jun Loh, Singapore (SG); Xiping Ni, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 13/654,251

(22) Filed: Oct. 17, 2012

(65) Prior Publication Data
US 2013/0095054 A1 Apr. 18, 2013

Related U.S. Application Data

(60) Provisional application No. 61/548,071, filed on Oct. 17, 2011.

(51) Int. Cl.
| | |
|---|---|
| *C11D 3/37* | (2006.01) |
| *C08F 220/34* | (2006.01) |
| *C08F 220/28* | (2006.01) |
| *A61Q 19/00* | (2006.01) |
| *A61K 8/91* | (2006.01) |
| *A61Q 5/00* | (2006.01) |

(52) U.S. Cl.
CPC .............. *C11D 3/3707* (2013.01); *A61K 8/91* (2013.01); *A61Q 19/00* (2013.01); *C08F 220/28* (2013.01); *C08F 220/34* (2013.01); *C11D 3/3715* (2013.01); *A61K 2800/10* (2013.01); *A61Q 5/00* (2013.01); *C08F 2438/01* (2013.01)

(58) Field of Classification Search
CPC ................. C11D 3/3707; C08F 220/34; C08F 2220/286; C08F 2220/287
See application file for complete search history.

(56) References Cited

U.S. PATENT DOCUMENTS

| | | | | |
|---|---|---|---|---|
| 4,931,522 A * | 6/1990 | Catena | .................. | C08F 220/34 526/292.2 |
| 6,689,856 B2 * | 2/2004 | L'alloret | .................. | A61K 8/91 526/264 |
| 6,878,754 B2 * | 4/2005 | L'Alloret | ................ | A61K 8/046 521/134 |
| 7,115,255 B2 * | 10/2006 | L'Alloret | ................ | A61K 8/042 424/78.02 |
| 2004/0197357 A1 * | 10/2004 | Heming | ............. | B01F 17/0028 424/401 |
| 2006/0116290 A1 * | 6/2006 | Heming | .................. | A01N 25/04 504/360 |
| 2011/0286957 A1 * | 11/2011 | Prieve | .................... | C12N 15/87 424/78.23 |
| 2011/0305767 A1 * | 12/2011 | Alexander | ........... | C12N 5/0068 424/497 |

FOREIGN PATENT DOCUMENTS

| | | | | |
|---|---|---|---|---|
| EP | 0583814 A1 * | 2/1994 | ............. | C04B 24/24 |
| EP | 0629649 A1 * | 12/1994 | ............... | A61K 8/91 |

OTHER PUBLICATIONS

Yamamoto, Shin-ichi, Joanna Pietrasik, and Krzysztof Matyjaszewski. "Temperature-and pH-responsive dense copolymer brushes prepared by ATRP." Macromolecules 41.19 (2008): 7013-7020.*
Hourdet, D., F. L'alloret, and R. Audebert. "Synthesis of thermoassociative copolymers." Polymer 38.10 (1997): 2535-2547.*
Aubrecht, Katherine B., and Robert B. Grubbs. "Synthesis and characterization of thermoresponsive amphiphilic block copolymers incorporating a poly (ethylene oxide-stat-propylene oxide) block." Journal of Polymer Science Part A: Polymer Chemistry 43.21 (2005): 5156-5167.*
Bastiat, Guillaume, Bruno Grassi, and Jeanne François. "Micellar copolymerization of associative polymers: Study of the effect of acrylamide on sodium dodecyl sulfate—poly (propylene oxide) methacrylate mixed micelles." Journal of colloid and interface science 289.2 (2005): 359-370.*
Petit, Laurence, et al. "Synthesis of graft polyacrylamide with responsive self-assembling properties in aqueous media." Polymer 48.24 (2007): 7098-7112.*
Taylor, Lloyd D., and Leon D. Cerankowski. "Preparation of films exhibiting a balanced temperature dependence to permeation by aqueous solutions—a study of lower consolute behavior." Journal of Polymer Science: Polymer Chemistry Edition 13.11 (1975): 2551-2570.*
Shahalom, Sheikh, et al. "Poly (DEAEMa-co-PEGMa): a new pH-responsive comb copolymer stabilizer for emulsions and dispersions." Langmuir 22.20 (2006): 8311-8317.*
Alexandridis, Paschalis. "Poly (ethylene oxide)/poly (propylene oxide) block copolymer surfactants." Current opinion in colloid & interface science 2.5 (1997): 478-489.*
Iatridi, Zacharoula, et al. "Self-assembly and drug delivery studies of pH/thermo-sensitive polyampholytic (A-co-B)-b-C-b-(A-co-B) segmented terpolymers." Soft Matter 7.23 (2011): 11160-11168.*
Remington's Pharmaceutical Sciences, Mack Publishing Co., Easton, Pa. (18th Ed., 1990).
Handbook of Pharmaceutical Excipients, American Pharmaceutical Association, Washington, D.C., (6$^{th}$ Ed., 2009).

* cited by examiner

*Primary Examiner* — Bethany P Barham
*Assistant Examiner* — Peter Anthopolos
(74) *Attorney, Agent, or Firm* — Womble Bond Dickinson (US) LLP

(57) ABSTRACT

Described herein are copolymers comprising at least one first water-soluble monomeric unit, at least one second water-soluble monomeric unit, and at least one monomeric unit containing a basic residue.

15 Claims, 7 Drawing Sheets

COPOLYMERS

CROSS-REFERENCE TO RELATED APPLICATIONS

This application claims the benefit of priority of U.S. provisional application No. 61/548,071, filed Oct. 17, 2011, the contents of it being hereby incorporated by reference in its entirety for all purposes.

FIELD OF THE INVENTION

The present disclosure relates to copolymers useful as rheology modifiers.

BACKGROUND OF THE INVENTION

Rheology modifiers are often used in formulations, such as detergents, paints and cosmetic products, e.g., hair and skin care products. Depending on the application, different types of rheology modifiers can be added to these formulations to tailor the theological properties of the product to obtain the desired flow characteristics (viscoelasticity) and sensorial effects.

Some classes of rheological modifiers include electrolytes and associative polymers. Electrolytes can be added to formulations, such as personal care formulations, which tend to be based on concentrated surfactant systems consisting of a mixture of anionics such as alkyl sulfates, amphoterics and other ingredients. Addition of electrolytes (typically NaCl) can cause a change in the micellar structure of the surfactant molecules, e.g., from spherical to rod-shaped units, which subsequently grow and form a "gel" network, thereby increasing the viscosity of the formulation. However, the addition of salt does not always give rise to optimum rheological characteristics and can result in formulations that are stringy and rubbery in appearance.

Associative polymers are water soluble polymers containing hydrophobic moieties (e.g., hydrocarbon groups). In surfactant systems, associative polymers can form network-like supramolecular structures at relatively lower polymer concentration due to non-covalent bonding interactions between hydrophobic moieties. Apart from the hydrophobic binding interactions, associative polymers can also be modified to include other forms of interactions with surfactant micelles, such as ion-dipole and/or ion-ion attractions, that can lead to the formation of a network-like supramolecular structure comprising, e.g., associative polymers, solvent, salts, and surfactants, resulting in an increase in the viscosity of the formulation.

Apart from the chemical composition of the rheology modifier, other factors can affect the viscosity of the rheology modifier/surfactant system, such as pH, the concentration of the surfactant, and the concentration of the rheology modifier.

One limitation of conventional rheology modifier/surfactant systems is that at high concentrations of the surfactant, the network-like structure between the surfactant and rheology modifier is disrupted, which can decrease the mixture's viscosity. Furthermore, conventional rheology modifier/surfactant systems can require high concentrations of the rheology modifier to achieve a desirable viscosity while maintaining acceptable sensorial characteristics.

Accordingly, there exists a need to provide an effective rheology modifier capable of increasing the viscosity of a surfactant system at low concentrations of surfactant and rheology modifier, enhancing the rheological stability of the formulation, and which provides desirable sensorial effects in various applications.

SUMMARY OF THE INVENTION

According to a first aspect, there is provided a copolymer comprising at least one first water-soluble monomeric unit, at least one second water-soluble monomeric unit, and at least one monomeric unit containing a basic residue, wherein the first water-soluble monomeric unit is different from the second water-soluble monomeric unit.

According to a second aspect, there is provided a formulation comprising at least one copolymer of the first aspect and at least one excipient.

According to a third aspect, there is provided a process for preparing a copolymer, said process comprising the steps of contacting a first water-soluble monomer represented by the Formula 1':

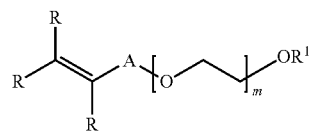

Formula 1' wherein m can be a whole number selected from 1-100; A can be —(C=O)— or a bond; and each R can be independently selected from the group consisting of hydrogen, alkyl, alkenyl, alkynyl, aralkyl, cycloalkyl, cycloalkenyl, heterocycloalkyl, and heterocycloalkenyl; and $R^1$ can be hydrogen, alkyl, alkenyl, alkynyl, aralkyl, cycloalkyl, cycloalkenyl, heterocycloalkyl, or heterocycloalkenyl; a second water-soluble monomer represented by the Formula 2':

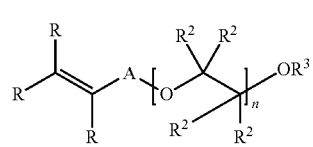

Formula 2' wherein n can be a whole number selected from 1-100; A can be —(C=O)— or a bond; each R can be independently selected from the group consisting of hydrogen, alkyl, alkenyl, alkynyl, aralkyl, cycloalkyl, cycloalkenyl, heterocycloalkyl, and heterocycloalkenyl; each $R^2$ can be independently selected from the group consisting of hydrogen, alkyl, alkenyl, alkynyl, aralkyl, cycloalkyl, cycloalkenyl, heterocycloalkyl, and heterocycloalkenyl; and $R^3$ can be hydrogen, alkyl, alkenyl, alkynyl, aralkyl, cycloalkyl, cycloalkenyl, heterocycloalkyl, or heterocycloalkenyl; wherein at least one $R^2$ cannot be hydrogen; and a monomer containing a basic residue represented by the Formula 3':

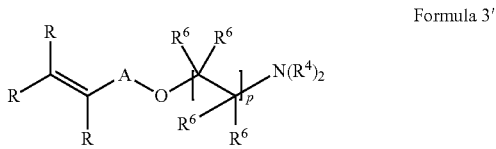

Formula 3' wherein p can be a whole number selected from 1-100; A can be —(C=O)— or a bond; and each R can be independently selected from the group consisting of hydrogen, alkyl, alkenyl, alkynyl, aralkyl, cycloalkyl, cycloalkenyl, heterocycloalkyl, and heterocycloalkenyl; and each $R^4$ can be independently selected from the group consisting of alkyl, alkenyl, alkynyl, aralkyl, cycloalkyl, cycloalkenyl, heterocycloalkyl, and heterocycloalkenyl; or two instances of $R^4$ taken together with the nitrogen to which they are attached form a 3 to 8 membered heterocylic ring; each $R^6$ can be independently selected from the group consisting of hydrogen, alkyl, alkenyl, alkynyl, aralkyl, cycloalkyl, cycloalkenyl, heterocycloalkyl, and heterocycloalkenyl; under polymerization conditions thereby yielding said copolymer.

Advantageously, as will be discussed in greater detail below, the copolymers described herein can form complex aggregates with ionic and/or polar molecules, such as water, surfactants, non-polar compounds, and other molecules of the copolymer. These intermolecular non-covalent bonding interactions can form an extended physical network between, e.g., molecules of the copolymer, surfactant, water, etc, which can increase the viscosity of the mixture. Importantly, it has been found that the copolymers described herein when used in connection with a surfactant, allow lower concentrations of the surfactant to be used while maintaining a desirable viscosity of the solution and improving the viscoelasticity properties and sensorial effects, e.g., visual and touch, or the solution or product.

BRIEF DESCRIPTION OF THE DRAWINGS

The invention will be better understood with reference to the detailed description when considered in conjunction with the non-limiting examples and the accompanying drawings, in which.

DEFINITIONS

Figure 1:
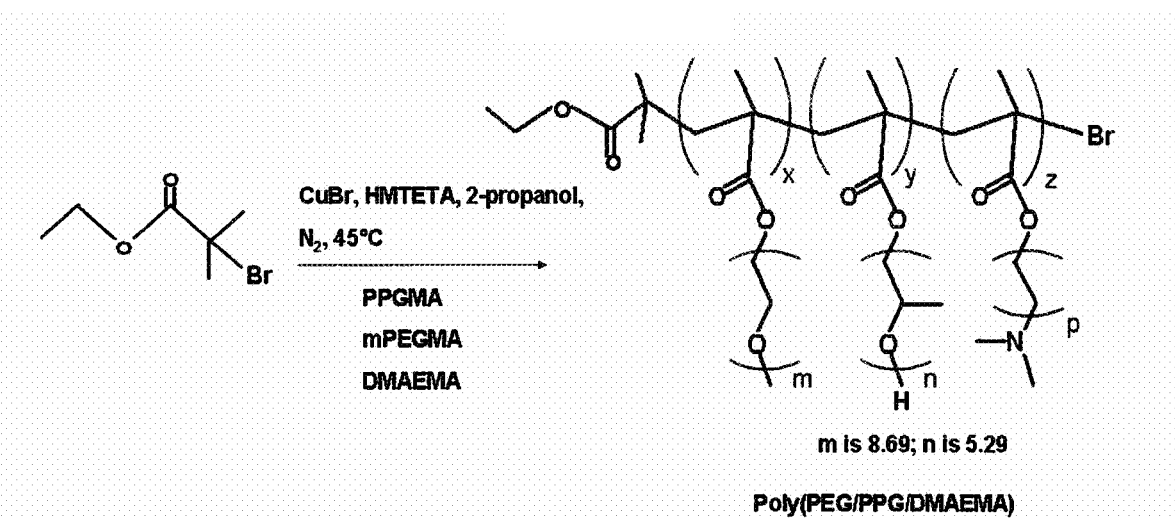
FIG. 1 depicts the synthetic scheme to the synthesis of brush-like copolymer with polyethylene glycol ("PEG"), polypropylene glycol ("PPG"), and poly(2-dimethylaminoethyl methacrylate ("PDMAEMA") side chains.

The following words and terms used herein shall have the meaning indicated:

As used herein, the term "alkyl group" includes within its meaning monovalent ("alkyl") and divalent ("alkylene") straight chain or branched chain saturated aliphatic groups having from 1 to 10 carbon atoms, eg, 1, 2, 3, 4, 5, 6, 7, 8, 9, or 10 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like.

The term "alkenyl group" includes within its meaning monovalent ("alkenyl") and divalent ("alkenylene") straight or branched chain unsaturated aliphatic hydrocarbon groups having from 2 to 10 carbon atoms, eg, 2, 3, 4, 5, 6, 7, 8, 9, or 10 carbon atoms and having at least one double bond, of either E, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pentenyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 1-nonenyl, 1-decenyl, and the like.

The term "alkynyl group" as used herein includes within its meaning monovalent ("alkynyl") and divalent ("alkynylene") straight or branched chain unsaturated aliphatic hydrocarbon groups having from 2 to 10 carbon atoms and having at least one triple bond anywhere in the carbon chain. Examples of alkynyl groups include but are not limited to ethynyl, 1-propynyl, 1-butynyl, 2-butynyl, 1-methyl-2-butynyl, 3-methyl-1-butynyl, 1-pentenyl, 1-hexynyl, methylpentynyl, 1-heptynyl, 2-heptynyl, 1-octynyl, 2-octynyl, 1-nonyl, 1-decynyl, and the like.

The term "cycloalkyl" as used herein refers to cyclic saturated aliphatic groups and includes within its meaning monovalent ("cycloalkyl"), and divalent ("cycloalkylene"), saturated, monocyclic, bicyclic, polycyclic or fused polycyclic hydrocarbon radicals having from 3 to 10 carbon atoms, eg, 3, 4, 5, 6, 7, 8, 9, or 10 carbon atoms. Examples of cycloalkyl groups include but are not limited to cyclopropyl, 2-methylcyclopropyl, cyclobutyl, cyclopentyl, 2-methylcyclopentyl, 3-methylcyclopentyl, cyclohexyl, and the like.

The term "aromatic group", or variants such as "aryl" or "arylene" as used herein refers to monovalent ("aryl") and divalent ("arylene") single, polynuclear, conjugated and fused residues of aromatic hydrocarbons having from 6 to 10 carbon atoms. Examples of such groups include phenyl, biphenyl, naphthyl, phenanthrenyl, and the like.

The term "aralkyl" as used herein, includes within its meaning monovalent ("aryl") and divalent ("arylene"), single, polynuclear, conjugated and fused aromatic hydrocarbon radicals attached to divalent, saturated, straight and branched chain alkylene radicals.

The term "optionally substituted" as used herein means the group to which this term refers may be unsubstituted, or may be substituted with one or more groups independently selected from alkyl, alkenyl, alkynyl, thioalkyl, cycloalkyl, cycloalkenyl, heterocycloalkyl, halo, carboxyl, haloalkyl, haloalkynyl, hydroxyl, alkoxy, thioalkoxy, alkenyloxy, haloalkoxy, haloalkenyloxy, nitro, amino, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, alkylheteroaryl, cyano, cyanate, isocyanate, —C(O)NH(alkyl), and —C(O)N(alkyl)$_2$.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

DETAILED DESCRIPTION OF THE PRESENT INVENTION

Exemplary, non-limiting embodiments of a copolymer, methods of for preparing a copolymer, and a formulation comprising a copolymer will now be disclosed.

The copolymer can be derived from the polymerization of at least one first water-soluble monomer, at least one second water-soluble monomer, and at least one monomer containing a basic residue.

The copolymer may comprise a plurality of monomeric units comprising at least one first water-soluble monomeric unit, at least one second water-soluble monomeric unit, and at least one monomeric unit containing a basic residue.

The copolymer can be an alternating copolymer, periodic copolymer, a statistical copolymer, a random copolymer, a block copolymer, or combinations thereof. The copolymer can be a block copolymer. The block copolymer can be a triblock, tetrablock, or pentabloek copolymer.

The copolymer can be a triblock copolymer comprising at least one first water-soluble monomeric unit, at least one second water-soluble monomeric unit, and at least one monomeric unit containing a basic residue.

The different monomeric units, e.g., the first water-soluble monomeric unit, the second water-soluble monomeric unit, and the monomeric unit containing a basic residue, can be present in the copolymer in any order.

In instances where the copolymer is a block copolymer, each monomer block can be present once in the copolymer or ran be present more than once, e.g., can be repeated on the copolymer 2, 3, 4, 5, 6, 7, 8, 9 or 10 times with other types of monomer blocks interspersed therebetween.

The copolymer can be a brush-like copolymer. Brush-like copolymers are characterized by a plurality of tethered polymers chains covalently attached to a polymer backbone. In instances where the tethered polymer chains are attached to the polymer backbone in close enough proximity to one and other, they are forced to stretch outwards from the polymer backbone to minimize steric interactions between adjacent tethered polymer chains. Typically, as the length of the tethered polymer chains approaches the distance between attachment points of the tethered polymer chains, the overall structure of the tethered polymers and the polymer backbone transitions to a more brush-like regime.

Depending on the hydrophilicity and/or charge of the outstretched tethered polymer chains, the micro-environment in the vicinity of the polymer backbone can be modified, e.g., can be made more hydrophilic, hydrophobic, and/or ionic in nature.

In instances, where the tethered polymer chains are hydrophilic in character, that portion of the copolymer is more likely to be exposed to water in aqueous solution.

Likewise, tethered polymer chains with ionic residues are more likely to interact with water and/or other charged species. In instances, where the tethered polymer chains are hydrophobic or less hydrophilic in character, that portion of the copolymer is more likely to interact with other hydrophobic or less hydrophilic groups.

In instances, where the copolymer is a block copolymer, each block of the copolymer can be modified with the appropriate functionality to affect the micro-environment of the copolymer in that block.

Without being bound by theory, it is believed that the copolymers of the present disclosure which can have well defined regions of hydrophilic, hydrophobic, and/or ionic character can form an extended supermolecular network in solution, which can include molecules of the copolymer, surfactant, solvent, and/or other molecules. As a result of this extended network, the viscosity of solutions comprising the copolymer can be substantially increased at low concentrations of the copolymer.

The first water-soluble monomeric unit can be selected such that it has higher water solubility than the second water-soluble monomeric unit, has lower water solubility than the second water-soluble monomeric unit, or has the substantially the same water solubility as the second water-soluble monomeric unit.

The solubility of the first water-soluble monomeric unit can be determined from the unpolymerized first water-soluble monomer and can be from 5 g/100 mL of water to being completely soluble in water at room temperature (25° C.). The solubility of the first water-soluble monomer can be greater than about 5 g/100 mL, greater than about 10 g/100 mL of water, greater than about 15 g/100 mL of water, greater than about 20 g/100 mL of water, greater than about 30 g/100 mL of water, greater than about 35 g/100 mL of water, greater than about 40 g/100 mL of water, greater than about 45 g/100 mL of water, or greater than about 50 g/100 mL of water at room temperature. The first water-soluble monomer can have a water solubility of about 50 g/100 mL to about 100 g/100 mL of water at room temperature. The first water-soluble monomer can be completely soluble in water, i.e., soluble in all proportions of the first water-soluble monomer to water at room temperature.

The first water-soluble monomeric unit can be a monomer comprising polyethylene glycol or alkoxylated polyethylene glycol. The alkoxylated polyethylene glycol can be terminated with a $C_1$-$C_6$, $C_1$-$C_5$, $C_1$-$C_4$, $C_1$-$C_3$, or $C_1$-$C_2$ alkyl ether. The alkoxylated polyethylene glycol can be terminated with a methyl ether.

The first water-soluble monomer can have a molecular weight of about 100 Da to about 800 Da; about 100 Da to about 700 Da; about 100 Da to about 600 Da; about 100 Da to about 400 Da; about 100 Da to about 300 Da; or about 100 Da to about 200 Da. The first water-soluble monomer can have a molecular weight of about 200 Da to about 600 Da; a molecular weight of about 300 Da to about 600 Da; a molecular weight of about 300 Da to about 500 Da; or a molecular weight of about 350 Da to about 450 Da.

The first water-soluble monomeric unit can be represented by the Formula 1:

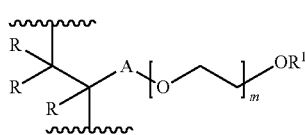

Formula 1 wherein m can be a whole number selected from 1-100; A can be —(C═O)— or a bond; and each R can be independently selected from the group consisting of hydrogen, alkyl, alkenyl, alkynyl aralkyl, cycloalkyl, cycloalkenyl heterocycloalkyl, and heterocycloalkenyl; and $R^1$ can be hydrogen, alkyl, alkenyl, alkynyl, aralkyl, cycloalkyl, cycloalkenyl, heterocycloalkyl, or heterocycloalkenyl.

A can be —(C═O)—. M can be any one of 2-90, 2-80, 2-70, 2-60, 2-50, 2-40, 2-30, 2-20, 2-10, 5-10, or 7-10.

$R^1$ can be hydrogen or alkyl. $R^1$ can be hydrogen, methyl, ethyl, propyl, butyl, pentyl, or hexyl.

Each R can be independently selected from the group consisting of hydrogen, alkyl, cycloalkyl, and aralkyl.

The first water-soluble monomeric unit can be represented by the Formula 1a:

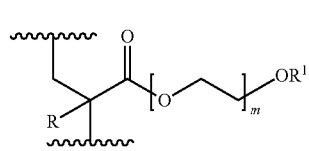

Formula 1a wherein m can be a whole number selected from 1-100; R can be hydrogen or alkyl and $R^1$ can be hydrogen or alkyl.

M can be any one of 2-90, 2-80, 2-70, 2-60, 2-50, 2-40, 2-30, 2-20, 2-10, 5-10, or 7-10. M can be 8 or 9.

R can be hydrogen or methyl. $R^1$ can be hydrogen, methyl, ethyl, propyl, butyl, pentyl, or hexyl.

R can be hydrogen or methyl; $R^1$ can be hydrogen or methyl; and m can be 7-10.

The solubility of the second water-soluble monomeric unit can be determined from the unpolymerized second water-soluble monomer and can be from 0.1 g/100 mL of water to being completely soluble in water at room temperature. The solubility of the second water-soluble monomer can be less than about 0.1 g/100 mL, less than about 0.2 g/100 mL of water, less than about 0.3 g/100 mL of water, less than about 0.4 g/100 mL of water, less than about 0.5 g/100 mL of water, less than about 0.6 g/100 mL of water, less than about 0.7 g/100 mL of water, less than about 0.8 g/100 mL of water, less than about 0.9 g/100 mL of water, or less than about 1 g/100 mL of water at room temperature. The second water-soluble monomer can have a water solubility of about 0.1 g/100 mL to about 2 g/100 mL of water, about 0.1 g/100 mL to about 1.5 g/100 mL of water, about 0.1 g/100 mL to about 1 g/100 mL of water, about 0.1 g/100 mL to about 0.9 g/100 mL of water, about 0.1 g/100 mL to about 0.8 g/100 mL of water, about 0.1 g/100 mL to about 0.7 g/100 mL of water, about 0.2 g/100 mL to about 0.7 g/100 mL of water, about 0.2 g/100 mL to about 0.6 g/100 mL of water, or about 0.3 g/100 mL to about 0.6 g/100 mL of water at room temperature. The second water-soluble monomer can have a solubility of about 0.5 g/100 mL to about 0.6 g/100 mL of water at room temperature.

The second water-soluble monomeric unit can be a monomer comprising an alkyl substituted polyethylene glycol or an alkyl substituted alkoxylated polyethylene glycol. The alkoxylated alkyl substituted polyethylene glycol can be terminated with a $C_1$-$C_6$, $C_1$-$C_5$, $C_1$-$C_4$, $C_1$-$C_3$, or $C_1$-$C_2$ alkyl ether. The alkoxylated alkyl substituted polyethylene glycol can be terminated with a methyl ether.

The second water-soluble monomer can have a molecular weight of about 100 Da to about 800 Da; about 100 Da to about 700 Da; about 100 Da to about 600 Da; about 100 Da to about 400 Da; about 100 Da to about 300 Da; or about 100 Da to about 200 Da. The second water-soluble monomer can have a molecular weight of about 200 Da to about 600 Da; a molecular weight of about 300 Da to about 600 Da; a molecular weight of about 300 Da to about 500 Da; a molecular weight of about 350 Da to about 450 Da; or a molecular weight of about 250 Da to about 400 Da.

The second water-soluble monomeric unit can be represented by the Formula 2:

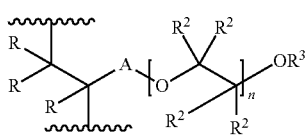

Formula 2 wherein n can be a whole number selected from 1-100; A can be —(C═O)— or a bond; each R can be independently selected from the group consisting of hydrogen, alkyl, alkenyl, alkynyl, aralkyl, cycloalkyl, cycloalkenyl, heterocycloalkyl, and heterocycloalkenyl each $R^2$ can be independently selected from the group consisting of hydrogen, alkyl, alkenyl, alkynyl, aralkyl, cycloalkyl, cycloalkenyl, heterocycloalkyl, and heterocycloalkenyl; and $R^3$ can be hydrogen, alkyl, alkenyl, alkynyl, aralkyl, cycloalkyl, cycloalkenyl, heterocycloalkyl, or heterocycloalkenyl; wherein at least one $R^2$ cannot be hydrogen.

A can be —(C═O)—. N can be any one of 2-90, 2-80, 2-70, 2-60, 2-50, 2-40, 2-30, 2-20, 2-10, 3-10, or 5-8.

$R^2$ can be hydrogen or alkyl.

$R^3$ can be hydrogen, methyl, ethyl, propyl, butyl, pentyl, or hexyl.

Each R can be independently selected from the group consisting of hydrogen, alkyl, cycloalkyl, and aralkyl.

The second water-soluble monomeric unit can be represented by the Formula 2a:

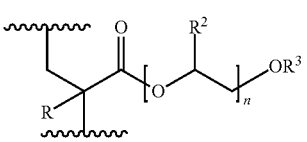

Formula 2a wherein n can be a whole number selected from 1-100; R can be hydrogen or alkyl; $R^2$ can be alkyl, cycloalkyl, or aralkyl; and $R^3$ can be hydrogen alkyl, cycloalkyl, or aralkyl. R can be hydrogen or methyl. $R^2$ can be alkyl. $R^3$ can be hydrogen or alkyl.

$R^3$ can be hydrogen, methyl, ethyl, propyl, butyl, pentyl, or hexyl.

N can be any one of 2-90, 2-80, 2-70, 2-60, 2-50, 2-40, 2-30, 2-20, 2-10, 5-10, or 5-8. N can be 5 or 6.

R can be hydrogen or methyl; $R^2$ can be alkyl; $R^3$ can be hydrogen or alkyl; and n can be 5-10.

The monomeric unit containing a basic residue can be a monomeric species, which contains a functional group capable of forming a positive charge upon protonation. Examples of such functional groups include, but are not limited to amines, admidines, guanidines, aromatic amines, such as optionally substituted pyridine, optionally substituted imidazole, optionally substituted pyrimidine, and phosphazenes.

In instances where the functional capable group capable of forming a positive charge can be an amine, any amine can be used including, but not limited to primary, secondary, and tertiary alkyl amines, aralkyl amines, alkenyl amines, alkynyl amines, cycloalkyl amines, cycloalkenyl amines, heterocycloalkyl amines, aryl amines, heteroaryl amines, heteroaralkyl amines, and 3-8 membered carbocylic amines.

The monomeric unit containing a basic residue may be present in the copolymer in the protonated state, unprotonated state, and combinations thereof.

The monomer containing a basic residue can have a molecular weight of about 100 Da to about 800 Da; about 100 Da to about 700 Da; about 100 Da to about 600 Da; about 100 Da to about 400 Da; about 100 Da to about 300 Da; or about 100 Da to about 200 Da. The monomer containing a basic residue can have a molecular weight of about 100 Da to about 600 Da; a molecular weight of about 100 Da to about 500 Da; a molecular weight of about 100 Da to about 400 Da; a molecular weight of about 100 Da to about 300 Da; or a molecular weight of about 100 Da to about 250 Da.

The monomeric unit containing a basic residue can be represented by the Formula 3 or its conjugate acid:

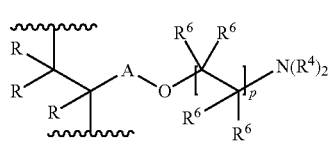

Formula 3 wherein p can be a whole number selected from 1-100; A can be —(C═O)— or a bond; and each R can be independently selected from the group consisting of hydrogen, alkyl, alkenyl, alkynyl, aralkyl, cycloalkyl, cycloalkenyl, heterocycloalkyl, and heterocycloalkenyl; and each $R^4$ can be independently selected from the group consisting of alkyl, alkenyl, alkynyl, aralkyl, cycloalkyl, cycloalkenyl, heterocycloalkyl, and heterocycloalkenyl; or two instances of $R^4$ taken together with the nitrogen to which they are attached form a 3 to 8 membered heterocylic ring; each $R^6$ can be independently selected from the group consisting of hydrogen, alkyl, alkenyl, alkynyl, aralkyl, cycloalkyl, cycloalkenyl, heterocycloalkyl, and heterocycloalkenyl.

A can be —(C═O)—. P can be any one of 1-20, 1-10, 1-8, or 1-6. P can be 1 or 2.

$R^6$ can be hydrogen.

Each $R^4$ can independently be alkyl. Two instances of $R^4$ taken together with the nitrogen to which they are attached can form a 3 to 8 membered heterocylic ring. $R^4$ can be a methyl, ethyl, propyl, butyl, or pentyl, hexyl. $N(R^4)_2$ can be an optionally substituted aziridine, optionally substituted azetidine, optionally substituted pyrrolidine, optionally substituted piperidine, optionally substituted morpholine, optionally substituted N-alkyl pipyrazine, or optionally substituted imidazole.

The monomeric unit containing a basic residue can be represented by the Formula 3a:

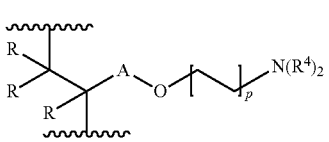

Formula 3a wherein p can be a whole number selected from 1-100; A can be —(C═O)— or a bond; and each R can be independently selected from the group consisting of hydrogen, alkyl, alkenyl, alkynyl, aralkyl, cycloalkyl, cycloalkenyl, heterocycloalkyl, and heterocycloalkenyl; and each $R^4$ can be independently selected from the group consisting of alkyl, alkenyl, alkynyl, aralkyl, cycloalkyl, cycloalkenyl, heterocycloalkyl, and heterocycloalkenyl; or two instances of $R^4$ taken together with the nitrogen to which they are attached form a 3 to 8 membered heterocylic ring.

Each R can be independently selected from the group consisting of hydrogen, alkyl, n cycloalkyl, and aralkyl.

The monomeric unit containing a basic residue can be represented by the Formula 3b:

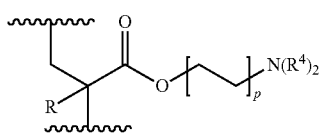

Formula 3b wherein p can be a whole number selected from 1-10; R can be hydrogen or alkyl; $R^4$ can be alkyl, cycloalkyl, or aralkyl; or two instances of $R^4$ taken together with the nitrogen to which they are attached can form a 3 to 6 membered heterocylic ring.

P can be any one of 1-10, 1-9, 1-8, 1-7, 1-6, 1-5, 1-4, 1-3, or 1-2. P can be 1.

The first water-soluble monomeric unit can be represented by the Formula 1:

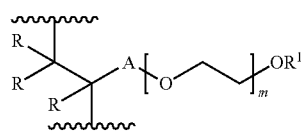

Formula 1 wherein m can be a whole number selected from 1-100; A can be —(C=O)— or a bond; and each R can be independently selected from the group consisting of hydrogen, alkyl, alkenyl, alkynyl, aralkyl, cycloalkyl, cycloalkenyl, heterocycloalkyl, and heterocycloalkenyl; and $R^1$ can be hydrogen, alkyl, alkenyl, alkynyl, aralkyl, cycloalkyl, cycloalkenyl, heterocycloalkyl, or heterocycloalkenyl; and the second water-soluble monomeric unit can be represented by the Formula 2:

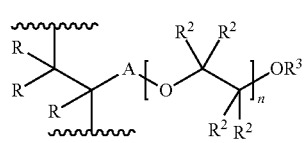

Formula 2 wherein n can be a whole number selected from 1-100; A can be —(C=O)— or a bond; each R can be independently selected from the group consisting of hydrogen, alkyl, alkenyl, alkynyl, aralkyl, cycloalkyl, cycloalkenyl, heterocycloalkyl, and heterocycloalkenyl; each $R^2$ can be independently selected from the group consisting of hydrogen, alkyl, alkenyl, alkynyl, aralkyl, cycloalkyl, cycloalkenyl, heterocycloalkyl, and heterocycloalkenyl; and $R^3$ can be hydrogen, alkyl, alkenyl, alkynyl, aralkyl, cycloalkyl, cycloalkenyl, heterocycloalkyl, or heterocycloalkenyl; wherein at least one $R^2$ can be not hydrogen; and the monomeric unit containing a basic residue can be represented by the Formula 3:

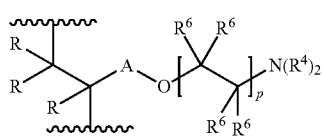

Formula 3 wherein p can be a whole number selected from 1-100; A can be —(C=O)— or a bond; and each R can be independently selected from the group consisting of hydrogen, alkyl, alkenyl, alkynyl, aralkyl, cycloalkyl, cycloalkenyl, heterocycloalkyl, and heterocycloalkenyl; and each $R^4$ can be independently selected from the group consisting of alkyl, alkenyl, alkynyl, aralkyl, cycloalkyl, cycloalkenyl, heterocycloalkyl, and heterocycloalkenyl; or two instances of $R^4$ taken together with the nitrogen to which they are attached form a 3 to 8 membered heterocylic ring; each $R^6$ can be independently selected from the group consisting of hydrogen, alkyl, alkenyl, alkynyl, aralkyl, cycloalkyl, cycloalkenyl, heterocycloalkyl, and heterocycloalkenyl; and wherein the first water-soluble monomeric unit, the second water-soluble monomeric unit, and the monomeric unit containing a basic residue can be present in the copolymer in any order.

M can be n can be 2-8; and p can be 1-6.

A can be —(C=O)—; each R can be independently selected from hydrogen and alkyl; and $R^4$ can be alkyl.

The ratio of the each of the monomeric units in the copolymer can be controlled by varying the ratio of the starting monomers used to prepare the copolymer. As such, the monomers can be present in the copolymer in any ratio.

The ratio of the first water-soluble monomeric unit to the second water-soluble monomeric unit can be between about 4:1 to about 1:4; about 4:1 to about 1:3; about 4:1 to about 1:2; about 4:1 to about 1:1; about 3:1 to about 1:1; to about 2.5:1 to about 1.5:1. In the examples below the first water-soluble monomeric unit and the second water-soluble monomeric unit are present in the copolymer in ratio from about 1.6:1 to about 2.5:1.

The molar ratio of the first water-soluble monomeric unit to the second water-soluble monomeric unit in the copolymer can be about 1:1 to about 3:1.

The monomeric unit containing a basic residue can comprise from about 0.01 mol % to about 80 mol % of the monomers in the copolymer. The monomeric unit containing a basic residue can comprise about 10 mol %, about 20 mol %, about 30 mol %, about 40 mol %, about 50 mol %, about 60 mol %, about 70 mol %, or about 80 mol % of the copolymer. The monomeric unit containing a basic residue can comprises between about 0.01 mol % to about 20 mol %; about mol % to about 30 mol %; about 30 mol % to about 40 mol %; about 40 mol % to about 50 mol %; or about 50 mol % to about 60 mol % of the copolymer.

The copolymer can comprise between about 0% to about 60% by weight of the monomeric unit containing a basic residue. The copolymer can comprise between about 0.01% to about 90%, about 5% to about 80%, about 10% to about 70%, about 20% to about 70%, about 30% to about 70%, about 40% to about 70%, or about 40% to about 60% by weight of the monomeric unit containing a basic residue.

The copolymer can be represented by a compound of Formula 4:

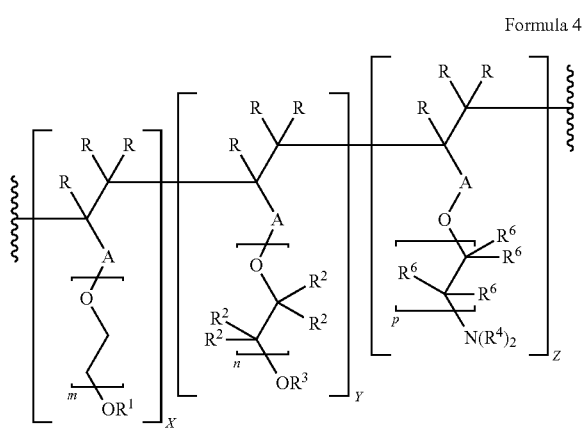

Formula 4 wherein m, n, p, R, A, $R^1$, $R^2$, $R^3$, $R^4$ and $R^6$ are as defined herein and X, Y, and Z represent the weight percentage of each monomer of Formulas 1, 2, and 3 present in the copolymer. X can be up to 5%, 10%, 15%, 20%, 25%, 30%, 35%, 45%, or 50% by weight of the copolymer. Y can be up to 5%, 10%, 15%, 20%, 25%, 30%, 35%, 45%, or 50% by weight of the copolymer. Z can comprise about 20 mol %, about 30 mol %, about 40 mol %, about 50 mol %, about 60 mol %, about 70 mol %, or about 80 mol % of the copolymer. Z can comprise between about 0 mol % to about 20 mol %; about 20 mol % to about 30 mol %; about 30 mol % to about 40 mol %; about 40 mol % to about 50 mol %; or about 50 mol % to about 60 mol % of the copolymer.

Although, the copolymer of Formula 4 is depicted as having the first water-soluble monomeric unit first, the second water-soluble monomeric unit second, and the monomeric unit containing the basic residue third, it is noted that copolymer can comprise monomeric units of Formula 1, 2, and 3 in any combination and/or order.

Depending on the amount and ratio of monomers used to prepare the copolymers described herein, the molecular weight of the polymer can be controlled. The copolymer can have a number average molecular weight of about 400,000 g/mol or less. The desired molecular weight of the copolymer can be controlled during the synthesis. The number average molecular weight of the copolymer can be about 350,000 g/mol or less; about 300,000 g/mol or less; about 250,000 g/mol or less; or about 200,000 g/mol or less.

The copolymer can have a number average molecular weight of about 10,000 g/mol to about 200,000 g/mol; 50,000 g/mol to about 200,000 g/mol; about 100,000 g/mol to about 200,000 g/mol; or about 150,000 g/mol to about 200,000 g/mol.

The copolymer can have a number average molecular weight of about 200,000 g/mol or less.

The copolymers described herein can exist as the free base or as an acid addition salt, e.g., formed by the reaction of a basic residue with an acid. The copolymer salt can be formed by reacting the copolymer with the appropriate acid or a salt of the monomer containing a basic residue can be copolymerized directly to form the copolymer salt.

If the copolymer exists as a salt, any where from one basic residue to all of the basic residues contained in the copolymer can be in protonated form.

Salts of the copolymers described herein can include those derived from inorganic acids such a hydrochloric acid, hydrobromic acid, sulfuric, sulfamic acid, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate.

In instances where the monomeric unit containing a basic residue comprises a basic nitrogen-containing groups, the nitrogen can be quarternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

The copolymers described herein can be prepared using any number of methods known to those skilled in the art. The copolymer can be prepared via the copolymerization of the corresponding unsaturated first water-soluble monomer, second water-soluble monomer, and monomer containing a basic residue, which can be represented by Formula 1', 2', and 3', respectively.

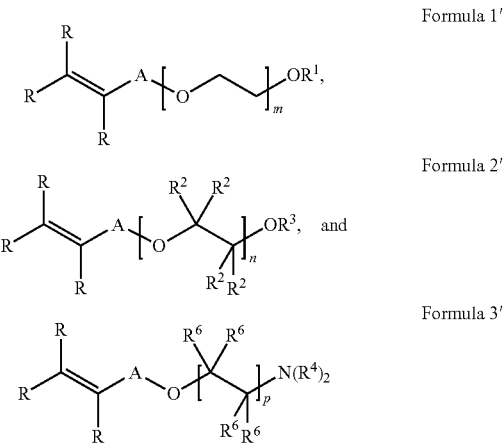

Formula 1'

Formula 2'

Formula 3' wherein m, n, p, $R^1$, $R^2$, $R^3$, $R^4$ and $R^6$ are as previously defined.

In instances where A is —(C=O)—, the compounds of Formula 1', 2', and 3' are substituted acrylates.

In instances where A is a bond, the compounds of Formula 1', 2', and 3' are substituted vinyl ethers.

Copolymerization of the monomers of Formula 1', 2', 3' can be accomplished using any of the various means known in the art, such as cationic polymerization, anionic polymerization, radical polymerization, photochemical polymerization, and electrochemical polymerization.

The copolymers can be prepared using a living (controlled) polymerization technique. Living polymerization techniques are useful methods for preparing well defined copolymers with a low polydispersity index. Living polymerization is a form of polymerization in which the ability of a growing polymer chain to terminate has been removed. Chain termination and chain transfer reactions are absent or very low and the rate of radical initiation is generally much larger than the rate of chain propagation. As a result of these conditions, the polymer chain can grow at a more constant rate as compared with traditional polymerization reactions and, in the case of block copolymers, each monomer block can be prepared sequentially. Depending on the nature of the copolymer that is desired, e.g., block copolymer, random copolymer, statistical copolymer, etc, the appropriate living polymerization technique can be employed to prepare the copolymer. Such living polymerization techniques include living anionic polymerization, living cationic polymerization, living free radical polymerization, living group-transfer polymerization, and living Ziegler-Nitta polymerization.

The copolymers be prepared by contacting the monomers described herein, e.g., monomers of Formula 1', 2', and 3', under polymerization conditions thereby forming the copolymer. Any polymerization condition known to those skilled in the art can be employed to prepare the copolymer, such as living anionic polymerization, living cationic polymerization, living free radical polymerization, such as atom transfer radical polymerization ("ATRP"), living group-transfer polymerization, and living Ziegler-Natta polymerization. In the examples below, the copolymers are prepared by using ATRP.

ATRP is an example of a living radical polymerization technique, which employs the use of a transition metal catalyst to mediate the formation of covalent bonds in a highly controlled process. ATRP reactions typically employ an organic halide initiator, an olefin monomer, and a transition metal catalyst.

The organic halide initiator can be an organic halide, such as iodide, bromide or chloride. Organic bromides tend to be more reactive and provide better results than organic chlorides. Typical organic halides include, but are not limited to alkyl halides, benzyl halides, α-halo esters, and α-halo amides.

Any organic halide initiator can be used in the preparation of the copolymers described herein. The organic halide initiator can be an alkyl halide, a benzyl halide, an α-halo ester, or an α-halo amide.

The organic halide initiator can be represented by a compound of Formula 6'

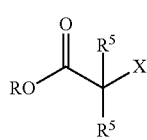

Formula 6' wherein X can be chloride or bromide; R can be alkyl, aralkyl, cycloalkyl, or heterocycloalkyl; and $R^5$ can be alkyl, aralkyl, cycloalkyl, or heterocycloalkyl. X can be bromide; R can be alkyl; and each $R^5$ can independently be alkyl.

In the examples below, ethyl α-bromoisobuterate is used as the organic halide initiator.

The copolymers described herein can further comprise an initiator attached at a terminal end of the copolymer, wherein the initiator can be represented by the Formula 6:

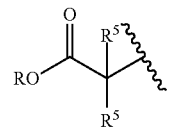

Formula 6 wherein R can be alkyl, aralkyl, cycloalkyl, or heterocycloalkyl; and $R^5$ can be alkyl, aralkyl, cycloalkyl, or heterocycloalkyl.

The copolymers described herein can further comprise an initiator attached at a terminal end of the copolymer, wherein the initiator can be α-isobuterate.

A broad range of transition metals can be used to catalyze ATRP reactions. Such transition metals include, but are not limited to Group IV metals, such as Ti, Group VI metals, such as Mo. Group VII metals, such as Re, Group VIII metals, such as Fe, Ru, and Os, Group LX metals, such as Rh and Co, Group X metals, such as Ni and Pd, and group XI metals, such as Cu.

Copper based ATRP catalysts exhibit broad functional group tolerance, good polymerization rates, and form well defined polymer products. Copper can be used in the +1 oxidation state or a copper precatalyst can be used to generate $Cu^{+1}$ in situ.

The catalyst counterion can be a halide ion, a pseudohalide, a carboxylate, triflate, or hexafluorophosphate.

The transition metal, e.g., copper, can be complexed with a nitrogenous ligand, such as derivatives of bidentate bipyridine (bpy) and pyridine imine, tridentate diethylenetriamine (DETA), and tetradentate tris[2-aminoethyl]amine (TREN) and tetraazacyclotetradecane (CYCLAM). In the examples below, copper is used in conjunction with 1,1,4,7,10,10-hexamethyltriethylenetetramine to prepare the ATRP catalyst.

The olefin monomer can be any monomer, e.g., those represented by Formulas 1', 2', 3', and combinations thereof.

ATRP reactions can be conducted in a broad range of solvents, such as benzene, toluene, xylene, tetrahydrofuran, 1,4-dioxane, anisole, dimethylformamide, dimethylsulfoxide, water, alcohols, such as methanol, ethanol, and isopropanol, acetonitrile, chloroform, and combinations thereof. In certain instances, the ATRP reaction can be conducted in a solvent consisting of the monomers employed in the copolymerization. In the examples below, the ATRP reaction is conducted in isopropanol.

In instances, where a block copolymer is prepared, the ATRP reaction can be conducted by contacting the organic halide initiator, the first monomer present in the desired block copolymer, and the transition metal catalyst under the appropriate reaction conditions for the ATRP reaction. The transition metal catalyst first reacts with the organic halide initiator to form an organometallic intermediate. This intermediate can then sequentially react by inserting into the double bone of the monomer to form a new carbon-carbon between the initiator and the monomer and carbon metal bond with the catalyst. This newly formed intermediate can continue to sequentially react with monomers by inserting into the olefin. In this way, the polymer chain continues to grow in length until substantially all of the first monomer is consumed in this fashion. After the first monomer is substantially consumed, the second monomer can be introduced into the reaction vessel and the second block of the copolymer can be built in the same fashion. This process can be repeated until the block copolymer has the desired number of blocks. Once the desired number of blocks has been achieved the reaction can be stopped and the desired product can be isolated as a block copolymer containing the organic initiator at a terminal end of the block copolymer and a transition metal residue, e.g., a halide, at the proximal end of the block copolymer.

In instances where the copolymer is a random or statistical copolymer, the copolymer can be prepared by adding the first water-soluble monomer, the second water-soluble monomer, and the monomer containing a basic residue to the reaction vessel where the ATRP reaction will be conducted at the same time.

If desired, the transition metal residue can be removed or chemically modified, e.g., the halide can be reacted with a reducing agent to replace it with hydrogen.

The copolymers described herein can further comprise a residue covalently attached at a terminal end of the copolymer, wherein the catalyst residue can be selected from chloride, bromide, or iodide.

The copolymer can have the Formula 5:

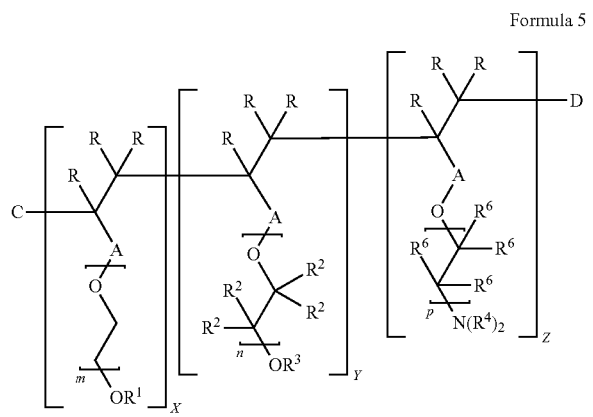

Formula 5 wherein m, n, p, R, A, $R^1$, $R^2$, $R^3$, $R^4$, $R^6$, X, Y, and Z are as defined herein and C and D can be selected from the group consisting of a residue selected from chloride, bromide, or iodide; and an initiator, wherein the initiator can be represented by the Formula 6:

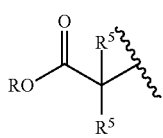

Formula 6 wherein R can be alkyl, aralkyl, cycloalkyl, or heterocycloalkyl; and $R^5$ can be alkyl, aralkyl, cycloalkyl, or heterocycloalkyl; wherein at least one of C or D can be a residue and at least one of C or D can be an initiator of Formula 6.

In the examples below, the copolymer is prepared by copolymerization of polyethylene glycol methacrylate, polypropylene methacrylate, and 2-(N,N dimethylamino) ethyl methacrylate, using a copper(I)bromide 1,1,4,7,10,10-hexamethyltriethylenetetramine catalyst in isopropanol at 45° C. under nitrogen.

Advantageously, the copolymers prepared using ATRP reaction can have a very low polydispersity index (PDI). The PDI of the copolymer can be from about 1.05 to about 2.0; about 1.05 to about 1.8; about 1.05 to about 1.6; or about 1.05 to about 1.6

Also provided, is a formulation comprising a copolymer as described herein and at least one excipient. The excipient can be any excipient useful in the formulation of pharmaceuticals, paints, detergents, cosmetics, such as hair care products, skin care products, and nail care products, and combinations thereof.

Acceptable excipients can include any substance used as a carrier, diluent, adjuvant, binder, and/or vehicle for delivery of an agent or substance and/or to improve its handling or storage properties or to permit or facilitate formation of a composition for an intended use.

Cosmetically acceptable excipients include preservatives, antioxidants, chelating agents, sunscreen agents, vitamins, dyes, hair coloring agents, proteins, amino acids, plant extracts, humectants, fragrances, perfumes, oils, emollients, lubricants, butters, penetrants, thickeners, viscosity modifiers, polymers, resins, hair fixatives, film formers, surfactants, detergents, emulsifiers, opacifying agents, volatiles, propellants, liquid vehicles, carriers, carriers, salts, pH adjusting agents, neutralizing agents, buffers, hair conditioning agents, anti-static agents, anti-frizz agents, anti-dandruff agents, hair waving agents, hair straightening agents, relaxers, absorbents, and combinations thereof.

Pharmaceutically acceptable excipient can mean any substance, not itself a therapeutic agent, used as a carrier, diluent, adjuvant, binder, and/or vehicle for delivery of a therapeutic agent to a subject, or added to a pharmaceutical composition to improve its handling or storage properties or to permit or facilitate formation of a compound or composition into a unit dosage form for administration. Pharmaceutically acceptable excipients are well known in the pharmaceutical arts and are described, for example, in Remington's Pharmaceutical Sciences, Mack Publishing Co., Easton, Pa. (e.g., 20.sup.th Ed., 2000), and Handbook of Pharmaceutical Excipients, American Pharmaceutical Association, Washington, D.C., (e.g., 1.sup.st, 2.sup.nd and 3.sup.rd Eds., 1986, 1994 and 2000, respectively). As will be known to those skilled in the art, excipients may provide a variety of functions and may be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose, and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The formulation can further comprise at least one surfactant. Any surfactant known to those skilled in the art can be used in combination with the copolymers described herein. Such surfactants include, but are not limited to anionic surfactants, cationic surfactants, nonionic surfactants, and amphoteric surfactants.

Examples of anionic surfactants include, but are not limited to alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, α-sulfofatty acid salts, N-acylamino acid surfactants, mono- or di-phosphate surfactants and sulfosuccinate salts.

The anionic surfactant can be an alkyl sulfonate having between about 10 to about 20 carbon atoms. Non-limiting examples of anionic surfactants include sodium dodecyl sulfate, sodium laureth sulfate, ammonium laurel sulfate, sodium lauryl sulfate, sodium myreth sulfate, dioctyl sodium sulfosuccinate, alkylbenze sulfonates, poly(ethylene glycol) 4-nonylphenyl 3-sulfopropyl ether potassium salt, sodium dodecylbenzenesulfonate, sodium coco fatty alcohol sulfate, sodium C14-C16 sulfonate, and sodium trideceth sulfate.

Examples of the counterion to the anionic residue of the above-described anionic surfactants include, but are not limited to alkali metal ions such as sodium ion and potassium ion, alkaline earth metal ions such as calcium ion and magnesium ion, ammonium ions, and alkanolamines having from 1 to 3 alkanol groups with 2 or 3 carbon atoms (such as monoethanolamine, diethanolamine, triethanolamine and triisopropanolamine).

Non-limiting examples of useful cationic surfactants include fatty amines; quaternary ammonium surfactants; and imidazoline compounds.

Examples of nonionic surfactants include, but are not limited to polyoxyalkylene alkyl ethers, polyoxyalkylene alkenyl ethers, higher fatty acid sucrose esters, polyglycerin fatty acid esters, higher fatty acid mono- or diethanolamides, polyoxyethylene hydrogenated castor oils, polyoxyethylene sorbitan fatty acid esters, polyoxyethylene sorbitol fatty acid esters, alkyl saccharide surfactants, alkylamine oxides, and alkyl amidoamine oxides.

Examples of amphoteric surfactants include, but are not limited to imidazolines, carbobetaines, amidobetaines, sulfobetaines, hydroxysulfobetaines, and amidosulfobetaines.

The formulation can comprise at least one copolymer as described herein and at least one surfactant.

The surfactant can be a sodium alkyl sulfate.

The formulation can comprise about 8% to about 25% by weight of sodium dodecyl sulfate.

The formulation can have a zero shear-rate viscosity or about 0.01 to about 20 Pa·s (1 Pa=1 kg/(m·s$^2$)). The formulation can have a shear-rate viscosity of about 0.01 to about 20 Pa·s, from about 2 to about 20 Pa·s; from about 5 to about 20 Pa·s, from about 5 to about 15 Pa·s, from about 5 to about 18 Pa·s, from about 5 to about 16 Pa·s, from about 5 to about 14 Pa·s, from about 5 to about 12 Pa·s, or from about 5 to about 10 Pa·s.

The shear-rate viscosity of the formulations described herein can change as a function of the pH of the formulation. In some instances, the shear-rate viscosity of the formulation increases as pH decreases.

The shear-rate viscosity of the formulation can increase about 50%, about 40%, about 30%, about 20%, or about 10% when the pH of the formulation is decreased pH 7 to pH 4.

The pH of the formulation can be between about 0 to about 14, from about 2 to about 10, from about 4 to about 8, from about 4 to about 7 or from about 4 to about 6. The pH of the formulation can be about 4.5 to about 5.5.

The pH of the formulation an be about 4 to about 6.

The shear-rate viscosity of the formulation can increase with increasing concentration of the copolymers described herein. Typically, the copolymer can be present in the formulation at about 0.5%, about 1.0%, about 1.5%, about 2.0%, about 2.5%, about 3.0%, about 3.5%, about 4.0%, about 4.5%, about 5.0%, about 5.5%, about 6.0%, about 6.5%, about 7.0%, about 7.5%, or about 8.0% by weight of the formulation.

The copolymer can be present in the formulation at about 0.5% to about 5%, about 1% to about 5%, about 2% to about 5%, or about 2% to about 4%, or about by weight of the formulation.

The formulation can comprise about 0.5% to about 3.0% by weight of the copolymer.

The formulation can further comprise a foam stabilizer. The foam stabilizer can be any foam stabilizer known to those skilled in the art, such as cetyl alcohol, cetearyl alcohol, stearic acid, and the like. Examples or skin care agents include guar gum, hydroxyethylcellulose, hydroxypropylmethylcellulose, polyethylene glycol, hydrolyzed wheat protein, polyoxyethylene stearyl ether, and the like. Other useful foam stabilizers also include the fatty amides, and particularly the mono- or diethanolamides of cocos fatty, acids, laurel- or oleic acid mono- or -diethanolamides.

The formulation can further comprise about 0.1% to about 10%, about 1% to about 10%, about 1% to about 9%, about 1% to about 8%, about 1% to about 7%, about 1% to about 6%, about 1% to about 5%, about 1% to about 4%, or about 1% to about 3% by weight of a foam stabilizer.

The formulation further can comprise about 2% to about 6% by weight of a foam stabilizer.

The formulations described herein can be used in the manufacture of a hair care product or a skin care product, or a paint.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Example 1

Preparation of Brush-like Copolymer Via Atom Transfer Radical Polymerization (ATRP)

The brush-like copolymer was synthesized via a controlled technique known as ATRP and subsequently purified before undergoing characterization methods such as gel permeation chromatography (GPC), $^1$H NMR and FTIR. The copolymers described herein can be synthesized through one-pot or multi-step ATRP reactions. In the examples below, the copolymer is formed using a one-pot ATRP method.

Firstly, a known amount of monomers (10 g) consisting of poly(propylene glycol) methacrylate ("PPGMA", typical $M_n$ of 375, Aldrich) and poly(ethylene glycol) methyl ether methacrylate ("mPEGMA", typical $M_n$ of 475, Aldrich) and 2-dimethylaminoethyl methacrylate ("DMAEMA", Merck, 99%) were weighed into a dry reaction flask, and dissolved in 18 mL of 2-propanol. The content of DMAEMA was varied from 0 to 80 mol % while the molar ratio of mPEGMA/PPGMA was maintained at 2.0 to create samples B-1 to B-7, as indicated in following Table 1.

TABLE 1

Selected characterization results for the brush-like copolymers

| # | Monomer Composition | | C [a] | Copolymer Composition [b] | | Molecular Weight, $M_n$ | | |
|---|---|---|---|---|---|---|---|---|
| | DMAEMA mol % | PEG/PPG mol/mol | % | PDMAEMA mol % | PEG/PPG mol/mol | $M_{n, predicted}$ [c] | $M_{n, GPC}$ [d] | PDI [d] |
| B-1 | 0 | 2.0 | 93 | 0 | 1.77 | 205K | (231 ± 22) K | 1.41 |
| B-2 | 20 | 2.0 | 92 | 19.84 | 1.99 | 177K | (197 ± 43) K | 1.45 |
| B-3 | 30 | 2.0 | 95 | 28.33 | 1.91 | 170K | (201 ± 20) K | 1.50 |
| B-4 | 50 | 2.0 | 81 | 49.75 | 2.37 | 160K | (164 ± 18) K | 1.26 |
| B-5 | 60 | 2.0 | 80 | 58.48 | 2.23 | 161K | (161 ± 15) K | 1.18 |
| B-6 | 70 | 2.0 | 83 | 69.44 | 2.38 | 166K | (169 ± 22) K | 1.41 |
| B-7 | 80 | 2.0 | 93 | 79.37 | 2.25 | 185K | (214 ± 24) K | 1.42 |

[a] The average monomer conversion was calculated according to the $^1$H NMR spectra of the ATRP reaction mixture after removal of copper catalyst;
[b] The copolymer composition was calculated according to the $^1$H NMR spectra of the final purified copolymer;
[c] The predicted $M_n$ was calculated based on the total weight of feed monomers, the feed initiator concentration and the average monomer conversion;
[d] The molecular weight and the polydispersity index (PDI) of the final copolymer were measured on Waters GPC system with differential refractive index and light scattering detectors.

The flask was subsequently sealed and purged using dry nitrogen for several minutes. Using a degassed syringe, ethyl α-bromoisobutyrate (Aldrich, 97%) (0.05 mmol, 9.8 mg) and 1,1,4,7,10,10-hexamethyltriethylenetetramine (HMTETA, Aldrich. 97%) (0.075 mmol, 17.3 mg) in thoroughly degassed 2-propanol were added as the initiator and ligand respectively. The mixture was stirred at room temperature and purged with dry nitrogen for 10 minutes. The catalyst copper(I) bromide (CuBr, Fluka, 98%) (0.05 mmol, 7.2 mg) was added and the mixture was purged with dry nitrogen for another 10 min at room temperature. The mixture was then heated at 45° C. under nitrogen atmosphere in an oil bath. The synthesis of the brush-like copolymer comprising PEG, PPG, and PDMAEMA is shown in FIG. 1.

The flask was re-opened again after 2 days, exposing the catalyst to air and the final green mixture was diluted with tetrahydrofuran (THF). The mixture was then filtered through an $Al_2O_3$ column to remove the copper catalyst and the filtrate was concentrated to 10 mL with further precipitation using 1 L of hexane/ether mix solvent. The sticky precipitate was collected, washed with 200 mL of hexane/ether mix solvent for about 3 to 4 times, and dried under vacuum.

During ATRP, the 3 monomers, mPEGMA, PPGMA and DMAEMA were copolymerized by following the above standard ATRP procedure in 2-propanol at 45° C. with varied feed ratio of $[M]_0/[I]_0$) and fixed feed ratio $[I]_0/[Cu]_0/[L]_0=1/1/1.2$ ($[M]_0$, $[I]_0$, $[Cu]_0$ and $[L]_0$ represent the feed molar ratios of mixed monomers, initiation sites, catalyst CuBr and ligand HMTETA, respectively).

Under the one-pot ATRP conditions, the typical average monomer conversion was about 90% based on $^1$H NMR analysis.

Example 2

Characterization of Brush-Like Copolymer Developed Via $^1$H NMR

Proton nuclear magnetic resonance ($^1$H NMR) spectra was recorded at room temperature on a Beaker Avance DRX 400 MHz NMR spectrometer operating at 400.1 MHz. Chemical shifts were reported in parts per million (ppm) on the δ scale, and were referenced to residual protonated solvent peaks: DMSO-$d_6$ spectra were referenced to ($CHD_2$) ($CD_3$)SO at δH 2.50; $CDCl_3$ spectra were referenced to $CHCl_3$ at δH 7.26.

The $^1$H NMR results of the brush-like copolymer were obtained as below: $^1$H NMR (400 MHz, $CDCl_3$, δ): 0.6-1.1 (b, —$CH_3$ on copolymer main chain), 1.1-1.4 (b, —$CHF_3$ on PPG side block). 1.5-2.1 (b, —$CH_2$ on copolymer main chain), 2.3 (s, —$N(CH_3)_2$ of PDMAEMA), 2.6 (s, —$CH_2$— N— of PDMAEMA). 3.2-3.8 (m, protons of PEG and PPG), 4.0-4.2 (b, protons adjacent to the ester bond).

Figure 2:
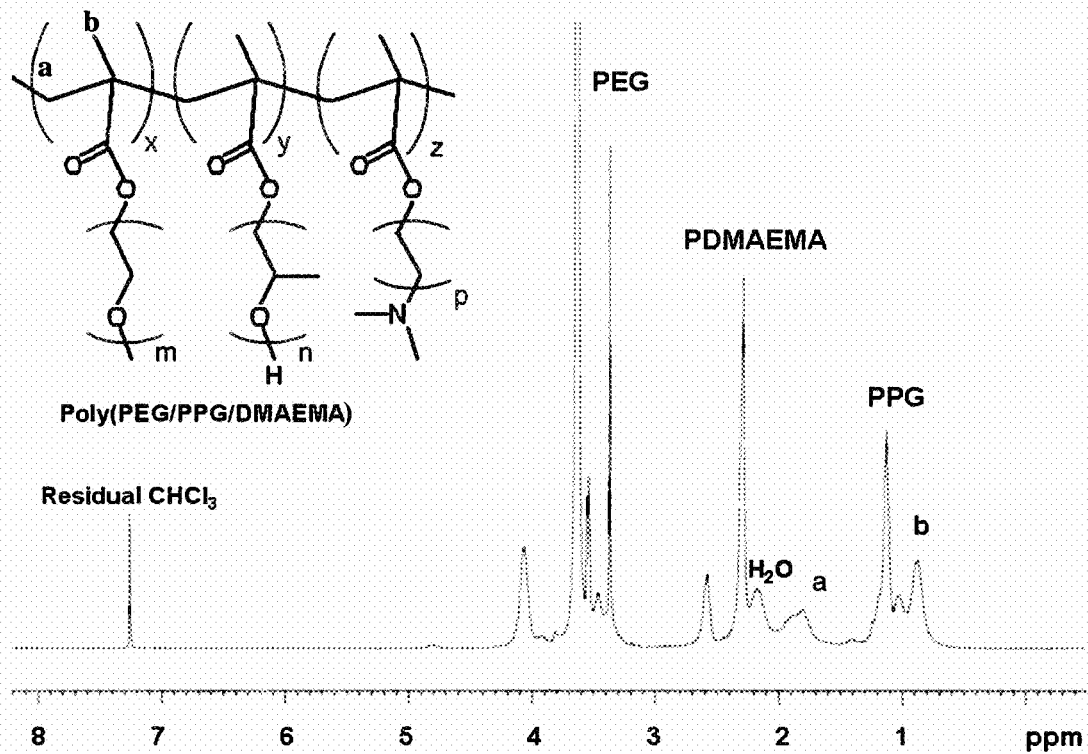
FIG. 2 shows the $^1$H NMR spectrum of brush-like copolymer B-4 synthesized via one-pot ATRP recorded in CDCl$_3$ at 400 MHz, 25° C. (molar ratio of PEG/PPG=2.37; content of PDMAEMA=49.75 mol % and 25.9 wt %).

Chemical composition of the final purified copolymer was determined by $^1$H NMR using integration ratio of resonances due to the protons adjacent to the ester bonds of all the three repeating units at the region 4.0 to 4.2 ppm, the protons of PEG and PPG at the region 3.2 to 3.8 ppm, the methylene protons of PDMAEMA at 2.6 ppm and all the methyl protons on the formed copolymer main chain and PPG side chains between 0.6 to 1.4 ppm. The typical $^1$H NMR spectrum of the synthesized brush-like copolymer from sample B-4 is shown in FIG. 2.

The average monomer conversion was also calculated from $^1$H NMR spectra (recorded in DMSO-$d_6$ or CDCl$_3$) of the final reaction mixture by comparing the integration of the vinyl protons of the remaining monomer in the region of 5.0 to 6.5 ppm to the overall integration of methyl proton signals between 0.6 to 1.4 ppm due to the formed polymer and the PPG side blocks.

Example 3

Characterization of Brush-like Copolymer Developed Via Polydispersity Index (PDI)

The number-average molecular weight ($M_n$) of the copolymer was predicted based on the total weight of feed monomers, the feed initiator concentration and the average monomer conversion. The molecular weight as well as the polydispersity index (PDI=$M_w/M_n$) of the obtained copolymers were further measured on a Waters system equipped with a Waters 2690 separations module, a Waters 410 differential refractive index detector and a Wyatt mini-DAWN light scattering detector. The characterization data for these copolymers were summarized in Table 1. The PDI values of the copolymers remained acceptable (<1.5) which is one of the indication that for all copolymerization performed, the final compositions remained very close to the initial monomer compositions.

Example 4

Characterization of Brush-like Copolymer Developed Via Gel Permeation Chromatography (GPC)

Figure 3:
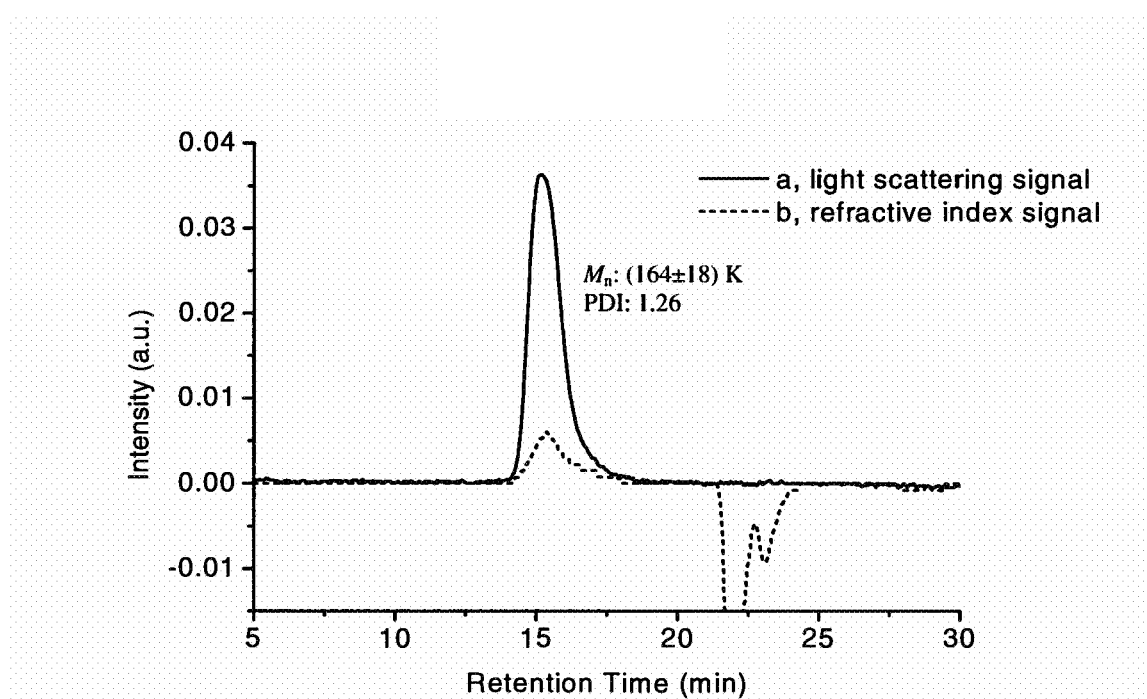
FIG. 3 shows the GPC elution curves of brush-like copolymer B-4 synthesised via one-pot ATRP, DMF containing 0.1 wt % LiBr as eluent with a flow rate of 1.0 mL/min at 25° C. (molar ratio of PEG/PPG=2.37; content of PDMAEMA=49.75 mol %, 25.9 wt %), (a) Light scattering signal, (b) refractive index signal.

GPC analysis was carried out with a Waters system equipped with a Waters 2690 separations module, a Waters 410 differential refractive index detector and a Wyatt mini-DAWN light scattering detector. HPLC-grade DMF containing 0.1 wt % LiBr was used as eluent at a flow rate of 1.0 mL/min at 25° C. Values of the molecular weight based on light-scattering measurement were found to correlate well with the predicted molecular weights from Table 1. Together with the PDI values, the results showed that the brush-like co-polymers of mPEGMA, PPGMA and DMAEMA were synthesized in controlled fashion by using the one-pot ATRP in this study. The corresponding GPC trace of sample B-4 is shown in FIG. 3.

Example 5

Characterization Brush-like Copolymer Developed Via FTIR

The FTIR spectra of samples deposited on surface of KBr plate were recorded on a Perkin-Elmer FTIR 2000 spectrometer in the region of 4000-400 cm$^{-1}$: 64 scans were signal-averaged with a resolution of 2 cm$^{-1}$ at room temperature. The FTIR results of the brush-like copolymer were obtained as below:
FTIR (KBr): ν(Nu)=3500 (br, ν(O—H)), 2945, 2874 (m, $ν_s$(C—H) and $ν_{as}$(C—H)), 1728 (s, ν(C=O), ester bond), 1456 (m), 1249 (m), 1151 (m, ν(C—N)), 1108 (m, ν(C—O—C)), 954 (m) cm$^{-1}$.

Figure 4:
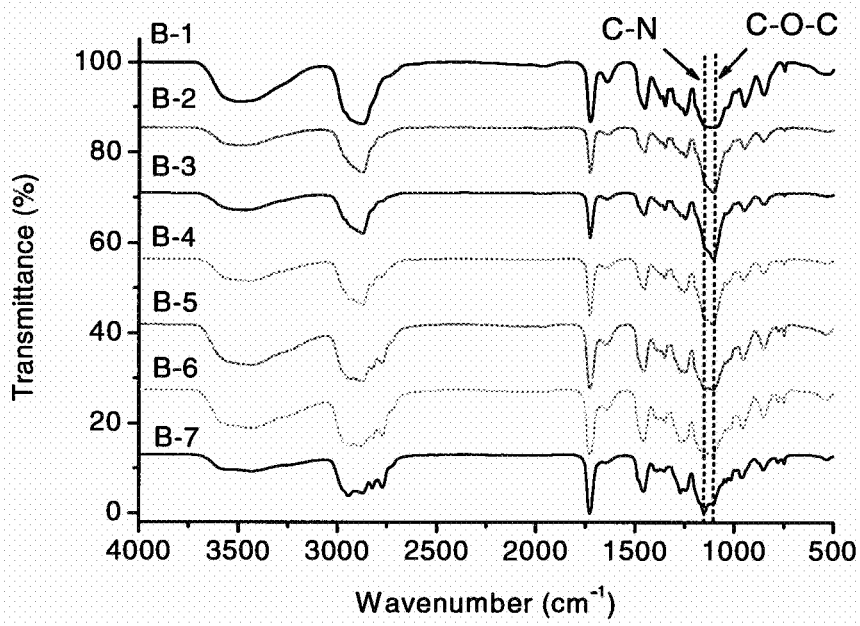
FIG. 4 shows the FTIR spectra of brush-like copolymers with different PDMAEMA content. B-1, 0%; B-2, 19.84 mol % (8.1 wt %); B-3, 28.33 mol % (12.4 wt %): 5-4, 49.75 mol % (25.9 wt %); B-5, 58.48 mol % (33.3 wt %); B-6, 69.44 mol % (44.5 wt %); B-7, 79.37 mol % (57.6 wt %), respectively.

The FTIR spectra of the series of brush-like copolymers with different PDMAEMA content are shown in FIG. 4.

From FIG. 4. It was found that for the copolymer containing no PDMAEMA, there was no absorption at 1151 cm$^{-1}$ corresponding to the C—N stretching of —N(CH$_3$)$_2$ group. While the absorption at 1108 cm$^{-1}$ due to the ether bonds (C—O—C) on PEG and PPG blocks was very strong. With increasing the content of PDMAEMA, the intensity of the absorption band at 1151 cm$^{-1}$ increased gradually, while intensity of the absorption band at 1108 cm$^{-1}$ decreased obviously. This observation from the FTIR spectra clearly showed the change in the chemical composition of the final copolymers.

Example 6

Preparation of Brush-like Copolymer/Surfactant Formulation

Samples for rheological study were then prepared by weighing a required amount of brush-like copolymer into the surfactant system, stirred at room temperature for 4 h until the mixture was homogenized, and then the pH of the mixture was adjusted to a required value (viable between 4.0 and 10.0 according to experimental requirements) with 1M HCl aqueous solution.

The brush-like copolymer/surfactant formulation was prepared by adding the brush-like copolymer (about 0.5 to 3.0 wt %), as prepared in Example 1, into a surfactant system comprising of SDS (Sigma Aldrich, 99%) with a content of about 8.0 to 25.0 wt % as a primary cleanser, coconut DEA (3B Pharmachem (China), 85%) with a constant viable content of 4.0 wt % as a foam stabilizer and water.

Example 7

Effect of Surfactant Concentration on Viscosity Measurements of the Copolymer/Surfactant Formulation The rheological tests were performed in an AR-G2 rheometer (TA instrument, USA), using cone-plate geometry (60 mm in diameter, steel cone). The viscosity of copolymer/surfactant mixture was measured over a range of shear rate 0.01-100 s$^{-1}$, and the zero shear-rate viscosity was calculated via best curve-fitting, which was used to evaluate the thickening effect of the brush-like copolymer in surfactant system.

Figure 5:
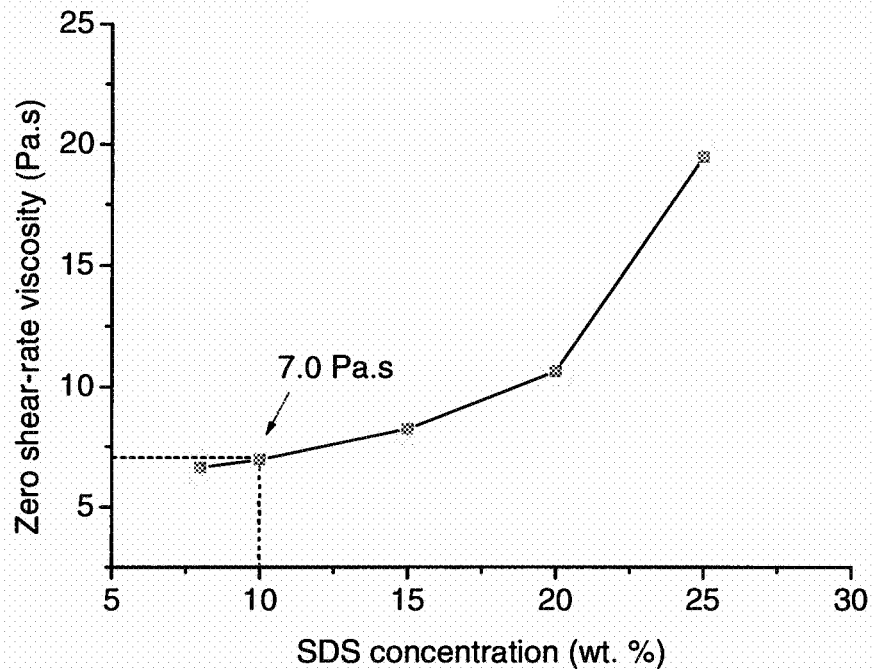
FIG. 5 shows the variation of zero shear-rate viscosity of the brush-like copolymer B-7/surfactant system as a function of SDS content at 25° C. and pH 6.0. Copolymer concentration: 2.0 wt %.

Surfactant systems with different SDS content (8.0-25.0 wt %) were thickened using the same amount of brush-like copolymer B-7 (copolymer concentration: 2.0 wt %). The zero shear-rate viscosity of these mixtures was measured at 25' C and pH close to 6.0 (the pH of the mixture was adjusted with 1M HCl aqueous solution). It was found from FIG. 5 that the zero shear-rate viscosity of the mixture increased obviously with increasing SDS concentration.

Example 8

Effect of pH on Viscosity Measurements of the Copolymer/Surfactant Formulation

The pH-dependent thickening property of this kind of brush-like copolymers in surfactant system was investigated. Cationic copolymer B-4 and B-5 with PDMAEMA content of 49.75 mol % (25.9 wt %) and 58.48 mol % (33.3 wt %), respectively were used for this study. Copolymer B-1, which contains no PDMAEMA was used as control. The mixture of cationic copolymer/surfactant system used in this study appeared basic with pH calculated at about 10 due to the amino groups on the PDMAEMA. By adding 1 M aqueous HCl solution, the amino side groups on the PDMAEMA was ionized, and the pH of the mixture reduced accordingly. Herein, a series of copolymer/surfactant mixtures with constant copolymer concentration (2.0 wt %) and variable pH value (about 4 to about 10) were prepared, and the zero shear-rate viscosity of these mixtures was measured at 25° C. (FIG. 6).

Figure 6:
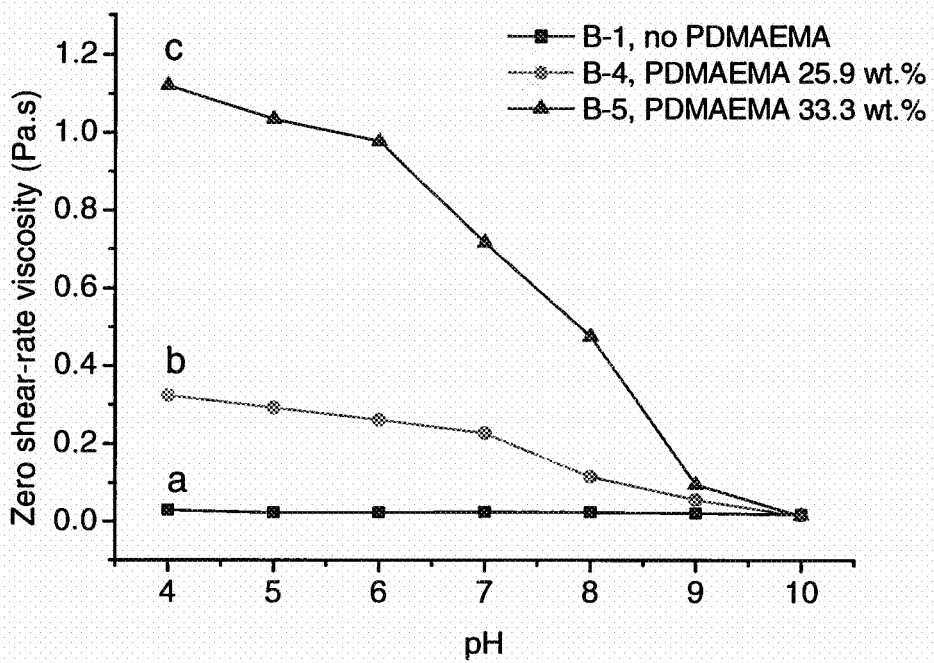
FIG. 6 shows the variation of zero shear-rate viscosity of the mixtures of brush-like copolymer/surfactant system as a function of pH value at 25° C. (a) Copolymer B-1 containing no PDMAEMA; (b) copolymer B-4 with PDMAEMA content of 49.75 mol % (25.9 wt %); (c) copolymer B-5 with PDMAEMA content of 58.48 mol % (33.3 wt %). Copolymer concentration: 2.0 wt %.

As shown in FIG. 6, a clear pH-dependent thickening effect was observed for the brush-like copolymers containing PDMAEMA in surfactant system (FIG. 6, curve b and c). By comparison, the copolymer B-1 containing no PDMAEMA did not show such effect (FIG. 6, curve a).

In the case of the brush-like copolymers containing PDMAEMA, firstly, a fast increase in viscosity of the copolymer/surfactant mixture was observed with descendant pH starting from the initial pH value of 10.0 (FIG. 6, curve b and c). Then, the increase in viscosity of the mixture became slow when the pH value reached 6.0.

FIG. 6 also showed that pH-dependent thickening effect of the copolymer in surfactant system was increased with a higher PDMAEMA content in the copolymer. In the case of copolymer B-4 with PDMAEMA content of 25.9 wt %, the zero shear-rate viscosity at pH of 6.0 was found to be 16-fold higher than the initial one at pH 10.0. However, in the case of copolymer B-5 with PDMAEMA content of 33.3 wt %, the zero shear-rate viscosity at pH of 6.0 was up to 65-fold higher than the initial one at pH 10.0.

Example 9

Effect of Cationic PDMAEMA Content on Viscosity Measurements of the Copolymer/Surfactant Formulation The influence of PDMAEMA content on the thickening performance of this kind of brush-like copolymers in surfactant system was also investigated. All the copolymers (B1 to B7) for this study possess similar molecular weight, similar PEG/PPG ratio, but varied PDMAEMA content (Table 1). The copolymer/surfactant mixtures with copolymer concentration of 2 wt % were prepared and measured at 25° C. and the pH of the mixtures were adjusted to 6.0 (FIG. 7).

Figure 7:
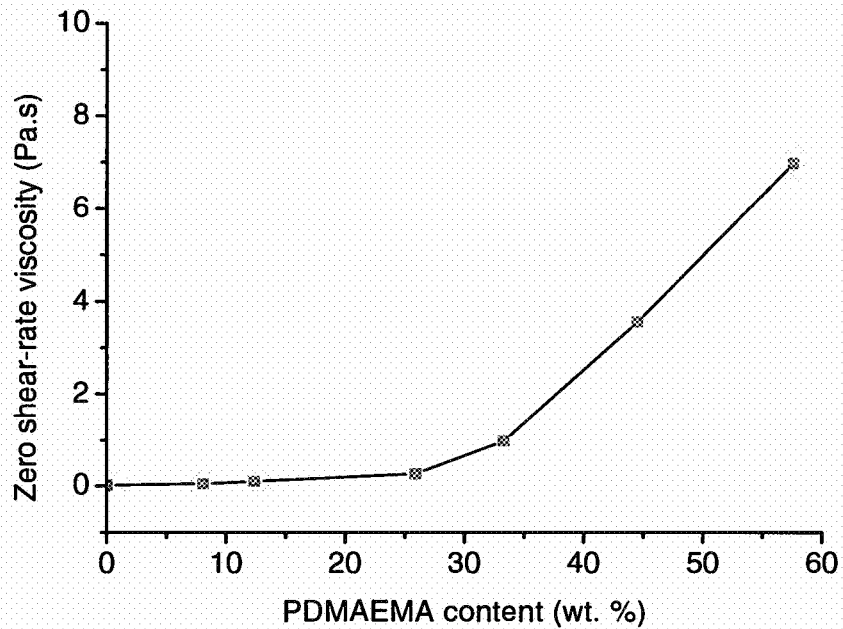
FIG. 7 shows the variation of zero shear-rate viscosity of the brush-like copolymer/surfactant mixtures as a function of PDMAEMA content. Concentration of copolymer: 2.0 wt %; 25° C.; pH 6.0.

It was seen from FIG. 7 that zero shear-rate viscosity of copolymer/surfactant mixture increased with increasing the content of cationic PDMAEMA. At first, this increase was slow in cases where the copolymer contained low amounts of PDMAEMA, such as in the range of 0 to 25 wt %. When the PDMAEMA content became higher than 25 wt % in the copolymer, the zero shear-rate viscosity of copolymer/surfactant mixture increased rapidly. Without being bound by theory, it is believed that this observation was related to the fact that, with increase in the content of cationic PDMAEMA in the copolymer, the ionization degree of copolymer main chain increased accordingly at fixed pH value of the mixture (6.0), which prompted the copolymer chain to extend into aqueous media to form physical network structure. On the other hand, the ionic interactions between brush-like copolymer chains and anionic micelles or aggregates formed by surfactant molecules were also enhanced, which contributed to the stability of the physical network structure.

Further study showed that the transparency of the copolymer/surfactant mixture also changed with PDMAEMA content at constant copolymer concentration of 2.0 wt % and pH value of 6.0. When PDMAEMA content is below 60 wt %, the mixture is transparent and homogeneous; when PDMAEMA content is higher than 60 wt %, the mixture began to turn semitransparent.

Example 10

Effect of Brush-like Copolymer Concentration on Viscosity Measurements of the Copolymer/Surfactant Formulation In this study, the concentration-dependent thickening property of this kind of brush-like copolymers in surfactant system was investigated at 25° C. and pH 6.0. The copolymers B-6 and B-7 with the PDMAEMA content of 69.44 mol % (44.5 wt %) and 79.37 mol % (57.6 wt %), respectively were used for this study (FIG. 8).

Figure 8:
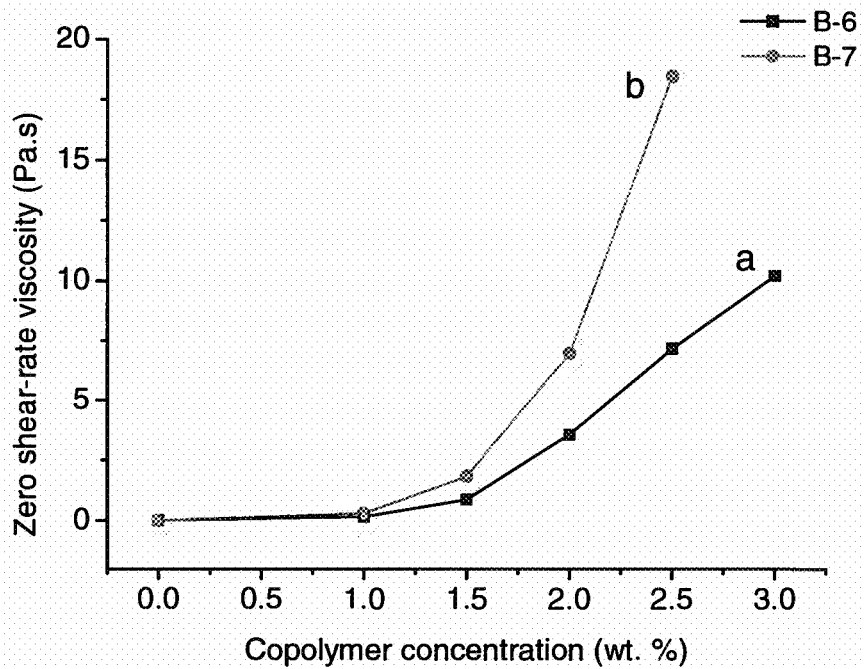
FIG. 8 shows the variation of zero shear-rate viscosity of the brush-like copolymer/surfactant mixtures as a function of copolymer concentration at 25° C. and pH 6.0. (a) Copolymer B-6 with the PDMAEMA content of 69.44 mol % (44.5 wt %); (b) copolymer B-7 with PDMAEMA content of 79.37 mol % (57.6 wt %).

It can be seen from FIG. 8 that both copolymer B-6 and B-7 showed obvious concentration-dependent thickening effect in surfactant system. That is under lower copolymer concentrations (0-1.0 wt %), the increase in viscosity of the copolymer/surfactant mixture with increasing the copolymer concentration was relatively slow, showing that the thickening effect of the copolymer in surfactant system was relatively weak under lower copolymer concentration.

However, once the copolymer concentration reached up to 1.0 wt %, the increase in viscosity of the mixture with increasing the copolymer concentration became very fast, showing that the thickening effect of the copolymer became very clear. This observation was corresponding to the building up of supermolecular aggregates (physical network structures) in the copolymer/surfactant mixture. The copolymer concentration where the copolymer/surfactant mixture showed a rapid increase in viscosity is the critical aggregation concentration (CAC). According to FIG. 8, the CAC is about 1.5 wt % for copolymer B-6 and B-7. By adjusting the copolymer concentrations, a bread zero-shear rate viscosity range of the copolymer/surfactant mixture can be achieved according to application requirement.

Example 11

Thickening Mechanism of Brush-like Copolymer in Surfactant System

Figure 9:
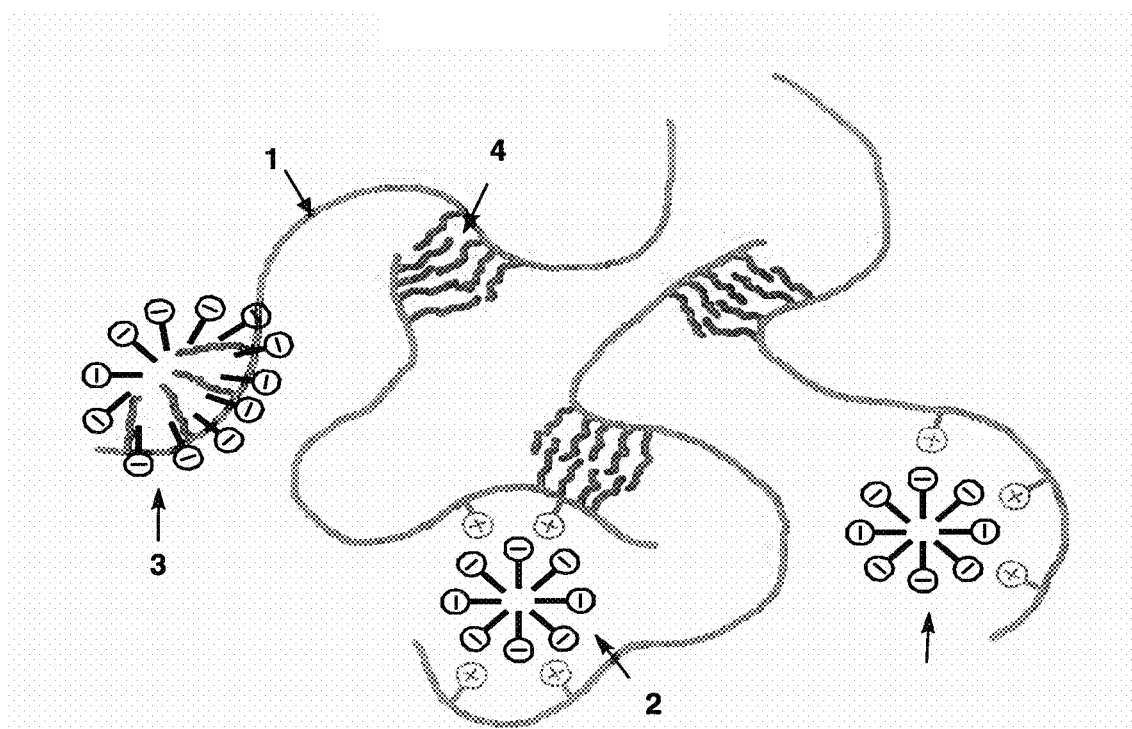
FIG. 9 depicts theoretical non-covalent interactions between different components of a rheology modifier/surfactant system, which are believed to lead to a thickening effect.

Not to be bound by theory and based on the examples above, the thickening mechanism for the brush-like copolymer in surfactant system was postulated as shown in FIG. 9. The copolymer backbone is indicated by 1 with the hydrophilic side chains being omitted for clarity. The copolymer/SDS mixed micelle complex formed via ionic interactions is being shown in 2 while 3 represents the copolymer/SDS mixed micelle formed by hydrophobic interactions. The intermolecular aggregation of two copolymer chains via hydrophobic interactions is represented by 4. Based on the various interactions postulated, one single copolymer molecule is able to participate in different noncovalent interactions, which can form an extended physical network that can result in a thickening effect.

Example 12

Comparison of the Thickening Performance Between the Developed Brush-like Copolymer and Salt for the Current Surfactant System Via Oscillatory Stress Test The comparative study was conducted using the surfactant system thickened with copolymer B-7 (copolymer concentration 2.0 wt %) and NaCl (salt concentration 2.0 wt %) at pH 6.0, respectively. Under this condition, the zero shear-rate viscosity of surfactant system thickened with NaCl was about 5.7 Pa·s, which was the maximum value this system could reach at the salt concentration range of 1.5-4.0 wt %. By comparison, the zero shear-rate viscosity of the same surfactant system thickened with copolymer B-7 could reach 7.0 Pa·s at the copolymer concentration 2.0 wt % and pH 6.0, showing that the thickening efficiency of the brush-like copolymer B-7 was better than NaCl.

Using the same rheological methodology from Example 7 to investigate the viscoelastic behavior, oscillatory measurements were performed for the two thickened surfactant systems mentioned above. Results were obtained as a function of applied stress (at constant frequency of 1 Hz) and frequency (whereby the strain or stress was fixed in the linear viscoelastic region).

Figure 10A:
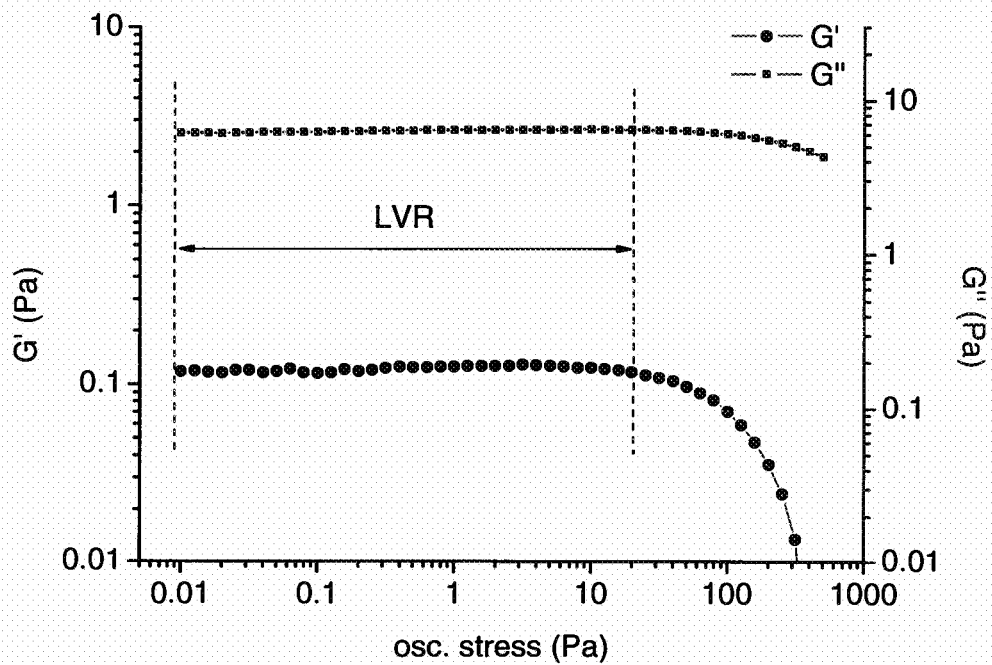
FIG. 10a shows the typical oscillatory stress sweep results obtained at 1 Hz for the surfactant system thickened win 2.0 wt % B-7 at 25° C.
Figure 10B:
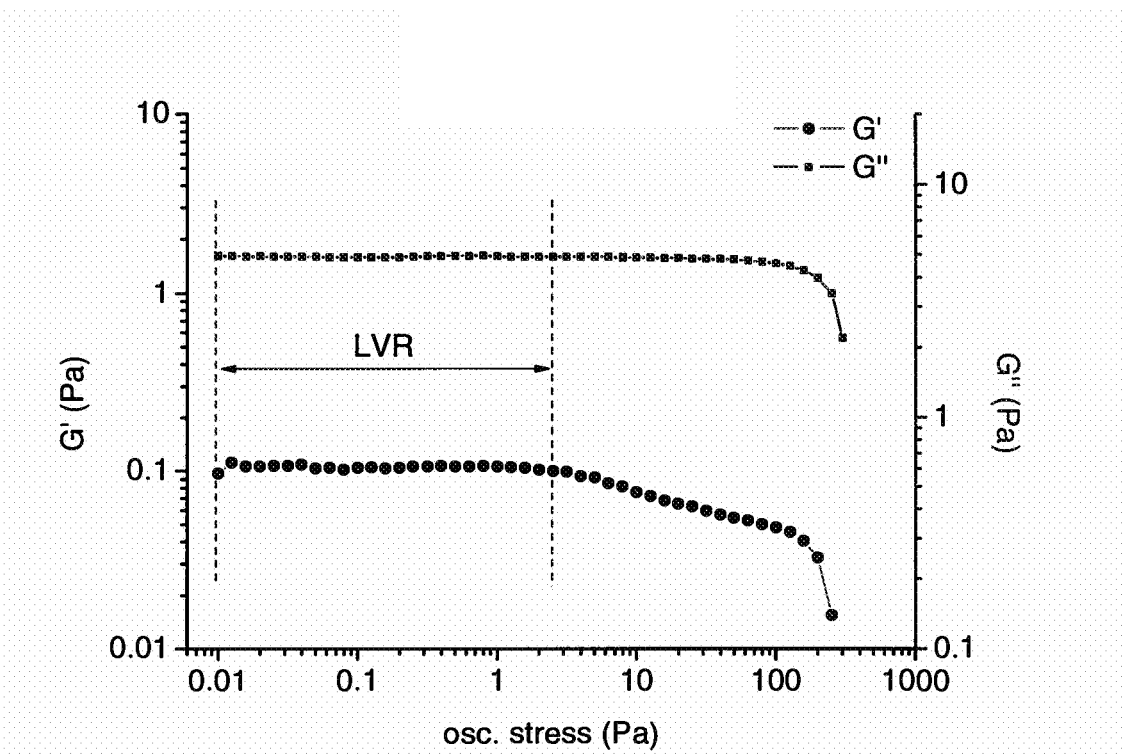
FIG. 10b shows the typical oscillatory stress sweep results obtained at 1 Hz for the surfactant system thickened with 2.0 wt % NaCl at 25° C.

FIG. 10 shows the typical oscillatory stress sweep results obtained at 1 Hz for the surfactant base thickened with (a) 2.0 wt % B-7 and (b) 2.0 wt % NaCl, respectively. In both cases G' and G" remained constant up to a critical stress, above which both G' and G" started to decrease with increasing oscillatory stress. Herein, the critical stress is the point at which a 5% change from the initial stable G' is occurred. The region below the critical stress at which G' and G" remain constant with increase in stress is denoted the linear viscoelastic region (LVR). It can be seen, that the surfactant system thickened with copolymer B-7 gave a longer LVR (0.01-20 Pa) compared with the system based on NaCl with a shorter LVR (0.01-2.5 Pa). This reflected the difference in network structure between the two systems, and the surfactant system thickened with copolymer B-7 (longer LVR) may give a more coherent network region than the system thickened with NaCl (shorter LVR).

Figure 11A:
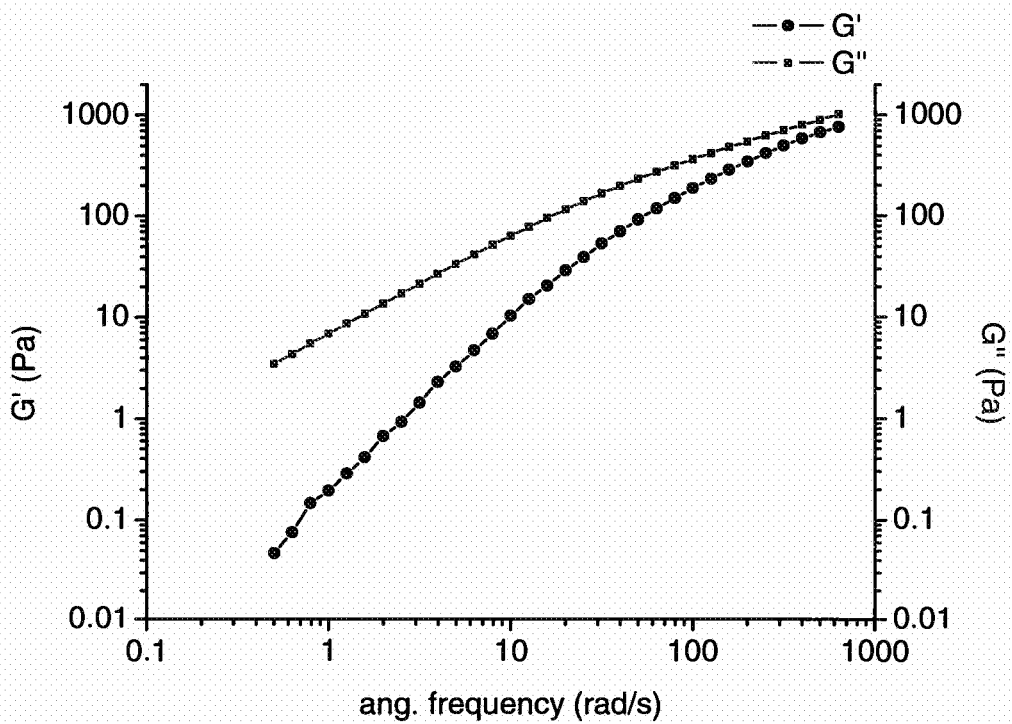
FIG. 11a shows the typical angular frequency sweep results obtained at 10% strain for the surfactant system thickened with 2.0 wt % B-7 at 25° C.
Figure 11B:
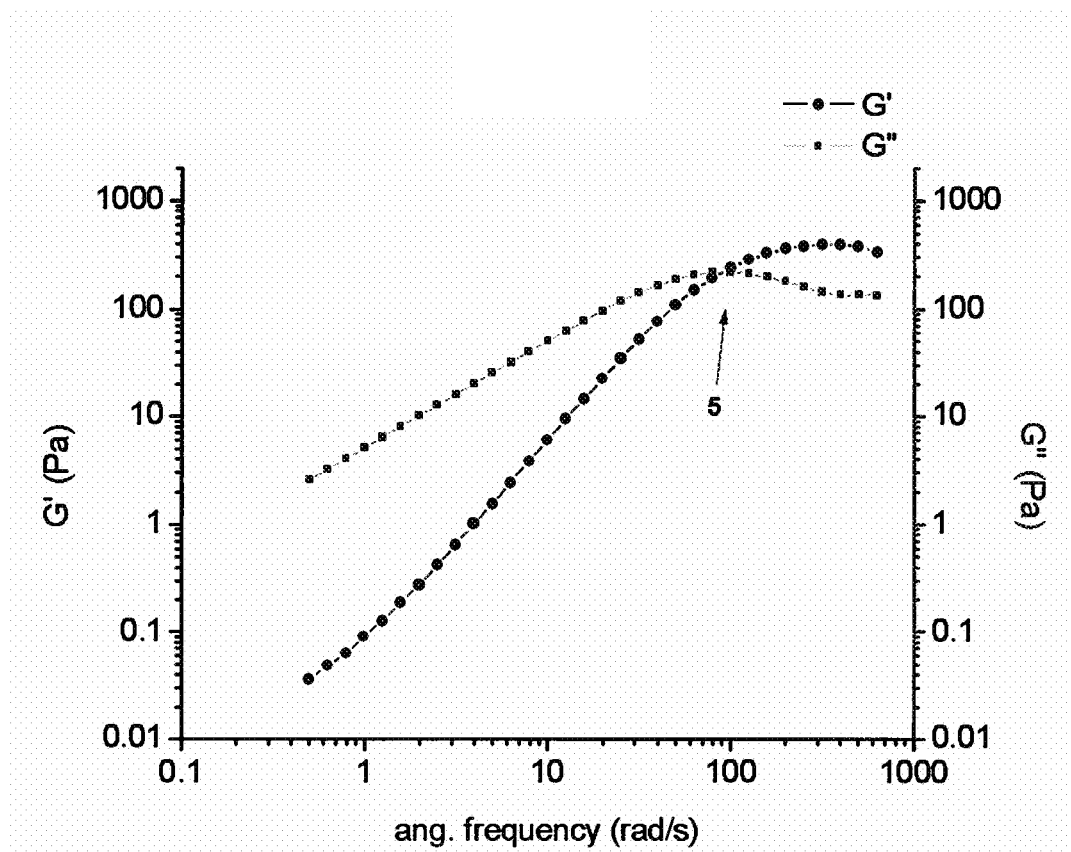
FIG. 11b shows the typical angular frequency sweep results obtained at 10% strain for the surfactant system thickened with 2.0 wt % NaCl at 25° C., where the cross over point occurs at a frequency of 90.76 rad/s and G is 217.16 Pa.

After the LVR was obtained, the effect of frequency on the two systems was measured. The typical frequency sweeps for the surfactant systems thickened with 2.0 wt % B-7 and 2.0 wt % NaCl are shown in FIG. 11 (a) and (b) respectively. The results showed a distinct difference between the two thickened systems. From FIG. 11b (the surfactant system thickened with NaCl), a cross-over point (at which G'=G" and indicated as 5) was observed at frequency 90.76 rad/s (G'=217.16 Pa). Below this critical frequency, the system was more viscous than elastic (G">G'), while above this critical frequency, the system began to appear elastic (G"<G'). By comparison, in FIG. 11a (the surfactant system thickened with copolymer B-7) no cross-over point was found in the angular frequency range of 0.5-628.3 raves. According to the curve trend, the cross-over point should occur at much higher frequency compared with the same base thickened with salt. This implied a much lower relaxation time for the B-7 thickened surfactant system compared with that thickened with salt, and this explained a better performance on surfactant systems thickened with B-7.

Applications

Rheology modifiers are useful for modulating the viscosity of aqueous solutions, organic solutions, and combinations thereof. Rheology modifiers can be used in a wide range of applications, such as in paint formulations, such as architectural paints, cosmetics such as nail, skin and hair care products, and cleansing formulations etc; to increase the viscosity of these systems.

The copolymer described herein can be used to change, e.g., increase, the viscosity of the surfactant systems by utilizing relatively low concentrations of copolymer (0.5 to 3 wt %) and surfactant, wherein the surfactant system comprises as little as about 8 to about 25 wt % surfactant, a foam stabilizer, such as coconut diethanolamide, and water. Compared to conventional electrolytes or associative polymers, the present copolymer is capable of achieving desirable viscosities with current surfactant systems at relatively low concentrations without giving rise to undesirable rheological characteristics and sensorial effects, such as becoming stringy or rubbery in appearance.

The copolymers disclosed herein also have additional advantages. For example, the incorporation of at least one monomeric unit containing a basic residue can contribute to the formation and stabilization of a network-like supramolecular structure in the surfactant system via intermolecular non-covalent interactions, such as Van Der Waals interactions, ion-ion interactions, ion dipole interactions, and dipole dipole interactions.

Further to this, the formulation of a copolymer as described herein and a surfactant can possess an optimum thickening effect in a pH range of about 4 to about 6, which is suitable for use in hair and skin care products. In addition, the zero shear-rate viscosity of the copolymer/surfactant system can change as a function of both the pH and/or the weight percentage of the monomeric unit containing the basic residue. Thus, the surfactant system's viscosity can be easily modified to meet the requirements of the desired application, such as in cosmetic products, detergents, paints and other suitable applications.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A copolymer comprising at least one first water-soluble monomeric unit, at least one second water-soluble monomeric unit, and at least one monomeric unit containing a basic residue, wherein the first water-soluble monomeric unit is different from the second water-soluble monomeric unit, and wherein the first water-soluble monomeric unit is represented by Formula 1a:

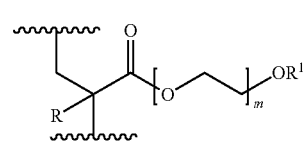

Formula 1a wherein m is 8 or 9;

R is hydrogen or methyl; and $R^1$ is hydrogen or methyl; and the second water-soluble monomeric unit is represented by Formula 2a:

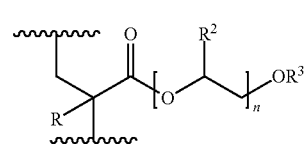

Formula 2a wherein n is 5 or 6;

R is hydrogen or methyl; $R^2$ is methyl; and $R^3$ is hydrogen or methyl; wherein the molar ratio of the first water-soluble monomeric unit to the second water-soluble monomeric unit in the copolymer is about 1:1 to about 3:1; and wherein the monomeric unit containing a basic residue is represented by the Formula 3b:

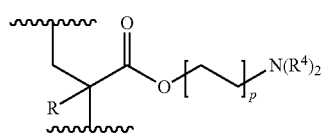

Formula 3b wherein p is a whole number selected from 1-10;

R is hydrogen or methyl; and each $R^4$ is independently selected from the group consisting of alkyl, alkenyl, alkynyl, aralkyl, cycloalkyl, cycloalkenyl, heterocycloalkyl, and heterocycloalkenyl; or two instances of $R^4$ taken together with the nitrogen to which they are attached form a 3 to 8 membered heterocylic ring; and wherein the first water-soluble monomeric unit, the second water-soluble monomeric unit, and the monomeric unit containing a basic residue are present in the copolymer in any order.

2. The copolymer of claim 1, wherein the copolymer is a brush-like copolymer.

3. The copolymer of any one of claim 1 or 2, wherein p is 1-6.

4. The copolymer of claim 1, wherein $R^4$ is alkyl.

5. The copolymer of claim 1, further comprising a catalyst residue covalently attached at a terminal end of the copolymer, wherein the catalyst residue is selected from chloride, bromide, or iodide.

6. The copolymer of claim 1, further comprising an initiator attached at a terminal end of the copolymer, wherein the initiator is represented by the Formula 6:

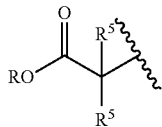

Formula 6 wherein

R is alkyl, aralkyl, cycloalkyl, or heterocycloalkyl; and $R^5$ is alkyl, aralkyl, cycloalkyl, or heterocycloalkyl.

7. The copolymer of claim 1, wherein the copolymer comprises between about 0% to about 60% by weight of the monomeric unit containing a basic residue.

8. The copolymer of claim 1, wherein the copolymer has a number average molecular weight of about 200,000 g/mol or less.

9. A formulation comprising at least one copolymer and at least one excipient, the copolymer comprising: at least one first water-soluble monomeric unit, at least one second water-soluble monomeric unit, and at least one monomeric unit containing a basic residue, wherein the first water-soluble monomeric unit is different from the second water-soluble monomeric unit, and wherein the first water-soluble monomeric unit is represented by Formula 1a:

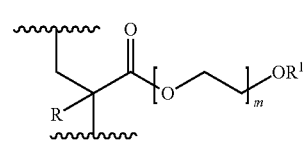

Formula 1a wherein m is 8 or 9;

R is hydrogen or methyl; and $R^1$ is hydrogen or methyl; and the second water-soluble monomeric unit is represented by Formula 2a:

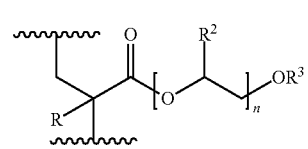

Formula 2a wherein n is 5 or 6;

R is hydrogen or methyl; $R^2$ is methyl; and $R^3$ is hydrogen or methyl;

wherein the molar ratio of the first water-soluble monomeric unit to the second water-soluble monomeric unit in the copolymer is about 1:1 to about 3:1; and wherein the monomeric unit containing a basic residue is represented by the Formula 3b:

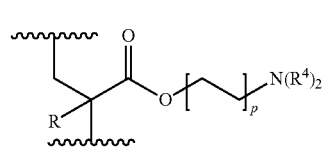

Formula 3b wherein p is a whole number selected from 1-10;

R is hydrogen or methyl; and each $R^4$ is independently selected from the group consisting of alkyl, alkenyl, alkynyl, aralkyl, cycloalkyl, cycloalkenyl, heterocycloalkyl, and heterocycloalkenyl; or two instances of $R^4$ taken together with the nitrogen to which they are attached form a 3 to 8 membered heterocylic ring;

and wherein the first water-soluble monomeric unit, the second water-soluble monomeric unit, and the monomeric unit containing a basic residue are present in the copolymer in any order, and wherein the formulation comprises about 0.5% to about 3.0% by weight of the copolymer.

10. The formulation of claim 9, further comprising at least one surfactant.

11. The formulation of claim 10, wherein the formulation comprises about 8% to about 25% by weight of the surfactant.

12. The formulation of claim 9, wherein the formulation has a zero shear-rate viscosity of about 0.01 to about 20 Pa·s.

13. The formulation of claim 9, further comprising about 2% to about 6% by weight of a foam stabilizer.

14. The formulation of claim 9, wherein the zero shear-rate viscosity changes as a function of the pH of the formulation.

15. The formulation of claim 9, wherein the pH of the formulation is about 4 to about 6.

* * * * *